(12) United States Patent
Park

(10) Patent No.: US 8,809,769 B2
(45) Date of Patent: Aug. 19, 2014

(54) APPARATUS AND METHOD FOR CROSS-FLOW ION MOBILITY SPECTROMETRY

(71) Applicant: Bruker Daltonics, Inc., Billerica, MA (US)

(72) Inventor: Melvin Andrew Park, Billerica, MA (US)

(73) Assignee: Bruker Daltonics, Inc., Billerica, MA (US)

( * ) Notice: Subject to any disclaimer, the term of this patent is extended or adjusted under 35 U.S.C. 154(b) by 0 days.

(21) Appl. No.: 13/688,594

(22) Filed: Nov. 29, 2012

(65) Prior Publication Data

US 2014/0145076 A1 May 29, 2014

(51) Int. Cl.
*H01J 49/00* (2006.01)

(52) U.S. Cl.
USPC ...................................................... 250/281

(58) Field of Classification Search
USPC ......... 250/281, 282, 283, 285, 286, 287, 288, 250/290, 293, 294
See application file for complete search history.

(56) References Cited

U.S. PATENT DOCUMENTS

| | | | |
|---|---|---|---|
| 4,542,293 A | 9/1985 | Fenn | |
| 5,283,436 A | 2/1994 | Wang | |
| 5,420,424 A | 5/1995 | Carnahan | |
| 5,572,035 A | 11/1996 | Franzen | |
| 5,763,878 A | 6/1998 | Franzen | |
| 5,844,237 A | 12/1998 | Whitehouse | |
| 5,847,386 A | 12/1998 | Thomson | |
| 5,905,258 A | 5/1999 | Clemmer | |
| 5,965,884 A | 10/1999 | Laiko | |
| 6,504,149 B2 | 1/2003 | Guevremont | |
| 6,630,662 B1 | 10/2003 | Loboda | |
| 6,777,672 B1 | 8/2004 | Park | |
| 6,903,334 B1 * | 6/2005 | Makarov et al. | 250/288 |
| 6,905,029 B2 | 6/2005 | Flagan | |
| 7,598,488 B2 | 10/2009 | Park | |
| 7,820,966 B2 | 10/2010 | Bateman | |
| 7,838,826 B1 | 11/2010 | Park | |
| 2004/0050756 A1 * | 3/2004 | Flagan | 209/156 |
| 2005/0006578 A1 * | 1/2005 | Rockwood et al. | 250/289 |

(Continued)

OTHER PUBLICATIONS

Schwartz, J., Senko, M. and Syka, J., "A Two-Dimensional Quadrupole Ion Trap Mass Spectrometer", Journal of the American Society for Mass Spectrometry, v. 13, pp. 659-669 (2002).

(Continued)

*Primary Examiner* — Michael Logie
*Assistant Examiner* — Jason McCormack
(74) *Attorney, Agent, or Firm* — O'Shea Getz P.C.

(57) ABSTRACT

A cross-flow ion mobility spectrometer consists of two parallel plates defining a volume between them. Analyte ions flow along an axis from an entrance end to an exit end through the volume. An RF confining field tends to guide ions along the axis. An analytical gas flow is established orthogonal to the axis. A DC electrostatic analytical field is oriented in opposition to the analytical gas flow such that the "drag force" on ions of the selected mobility due to the analytical gas flow is balanced by the force on the ions due to the electrostatic analytical field. The selected ions are thereby able to follow a stable path to the exit end of the cross-flow mobility analyzer. However, the force on ions of other than the selected mobility is unbalanced and these ions are deflected and lost.

14 Claims, 9 Drawing Sheets

(56) References Cited

U.S. PATENT DOCUMENTS

| | | | | |
|---|---|---|---|---|
| 2005/0029445 | A1* | 2/2005 | Lee et al. | 250/288 |
| 2007/0284519 | A1* | 12/2007 | Rockwood et al. | 250/282 |
| 2009/0134321 | A1* | 5/2009 | Hoyes | 250/282 |
| 2009/0272891 | A1* | 11/2009 | Giles | 250/282 |
| 2010/0108879 | A1 | 5/2010 | Bateman et al. | |
| 2011/0091864 | A1 | 4/2011 | Karlsson et al. | |
| 2011/0095175 | A1 | 4/2011 | Bateman | |
| 2011/0266435 | A1* | 11/2011 | Hoyes et al. | 250/282 |
| 2012/0273670 | A1* | 11/2012 | Park et al. | 250/282 |
| 2012/0273673 | A1 | 11/2012 | Park | |
| 2012/0273674 | A1 | 11/2012 | Park | |
| 2012/0305758 | A1 | 12/2012 | Park | |
| 2013/0306858 | A1* | 11/2013 | Giles et al. | 250/283 |
| 2014/0048696 | A1* | 2/2014 | Giles et al. | 250/281 |

OTHER PUBLICATIONS

Hager, J. W., "A New Linear Ion Trap Mass Spectrometer", Rapid Communications in Mass Spectrometry, v. 16, pp. 512-526 (2002).

Kingdon, K. H., "A Method for the Neutralization of Electron Space Charge by Positive Ionization at Very Low Gas Pressures", Physical Review, v. 21, pp. 408-418 (1923).

Hu, Q., Noll, R. J., Li, H., Makarov, A., Hardman, M. and Cooks, R.G. "The Orbitrap: A New Mass Spectrometer", Journal of Mass Spectrometry, v. 40, pp. 430-443 (2005).

Torgerson, D.F., Skowronski, R.P. and MacFarlane, R.D., "New Approach to the Mass Spectroscopy of Non-volatile Compounds", Biochemical and Biophysical Research Communications, v. 60, n. 2, pp. 616-621 (1974).

Vanbreeman, R.B., Snow, M. and Cotter, R.J., "Time Resolved Laser Desorption Mass Spectrometry.—I Desorption of Preformed Ions", International Journal of Mass Spectrometry and Ion Physics, v. 49, pp. 35-50 (1983), Elsevier Scientific Publishing Company, Amsterdam, Netherlands.

Tabet, J.C. and Cotter, R.J., "Laser Desorption Time-of-Flight Mass Spectrometry of High Mass Molecules", Analytical Chemistry, v. 56, pp. 1662-1667 (1984).

Tanaka, K., Waki, H., Ido, Y., Akita, S., Yoshida, Y. and Yoshica, T., "Protein and Polymer Analyses up to m/z 100 000 by Laser Ionization Time-of-flight Mass Spectrometry", Rapid Communications in Mass Spectrometry, v. 2, n. 8, pp. 151-153 (1988).

Karas, M. and Hillenkamp, F., "Laser Desorption Ionization of Proteins with Molecular Masses Exceeding 10 000 Daltons", Analytical Chemistry, v. 60, pp. 2299-2301 (1988).

Dole, M., Mack, L.L., Hines, R.L., Mobley, R.C., Ferguson, L.D. and Alice, M.B., "Molecular Beams of Macroions", The Journal of Chemical Physics, v. 49, n. 5, pp. 2240-2249 (1968).

Olthoff, J.K., Lys, I., Demirev, P. and Cotter, R.J., "Modification of Wiley-McLaren TOF Analyzers for Laser Desorption", Analytical Instrumentation, v. 16, n. 1, pp. 93-115 (1987).

Chernushevich, I.V., Ens, W. and Standing, K.C., "Orthogonal Injection TOFMS for Analyzing Biomolecules", Analyical Chemistry News and Features, v. 71, n. 13, pp. 452A-461A (1999).

Buryakov, et al., "A New Method of Separation of Multi-Atomic Ions by Mobility at Atmospheric Pressure Using a High-Frequency Amplitude-Asymmetric Strong Electric Field", Int'l J of Mass Spectrom and Ion Processes, 128 (1993) 143-148, Elsevier Science Publishers B.V.

Reigner, et al., "Qualitative Evaluation of Field Ion Spectrometry for Chemical Warfare Agent Detection", 45th ASMS Conference on Mass Spectrometry and Allied Topics, Jun. 1-5, 1997, Palm Springs, CA, US.

Srebalus, et al., "Gas-Phase Separations of Electrosprayed Peptide Libraries", Anal. Chem. 1999, 71, 3918-3927.

Taraszka, et al., "Mapping the Proteome of *Drosophila melanogaster*: Analysi of Embryos and Adult Heads by LC-IMS-MS Methods", J Proteome Research 2005, 4, 1223-1237.

Shvartsburg, et al., "Optimization of the Design and Operation of FAIMS Analyzers", J Am Soc Mass Spectrom 2005, 16, 2-12, Elsevier Inc.

Barnett, et al., "Application of ESI-FAIMS-MS to the Analysis of Tryptic Peptides", J Am Soc Mass Spectrom 2002, 13, 1282-1291, Elsevier Science Inc.

Page, et al., "Variable Low-Mass Filtering Using an Electrodynamic Ion Funnel", J Mass Spectrom 2005, 40 1215-1222, John Wiley & Sons, Ltd.

Zeleny, John, "On the The Ratio of the Velocities of the Two Ions producted in Gases by Rontgen Radiation; and on some Related Phenomena", philosophical Magazine, No. 46, pp. 120-154. (1898).

Wong, et al., "Evaluation of Ion Mobility Spectroscopy for Determining Charge-Solvated Versus Salt-Bridge Structures of Protonated Trimers", Am Soc Mass Spectrom 2005, 16, 1009-1019, Elsevier Inc.

Tammet, H. "The Limits of Air Ion Mobility Resolution." Proceedings of 11th International Conference on Atmospheric Electricity, NASA, MSFC, Alabama, pp. 626-629 (1999).

Tammet, H., "Symmetric Inclined Grid Mobility Analyzer for the Measurement of Charged Clusters and Fine Nanoparticles in Atmospheric Air", Aerosol Science and Technology, v. 45, pp. 468-479 (2011).

Agbonkonkon, N., "Counter-flow Ion Mobility Analysis: Design, Instrumentation, and Characterization", Ph.D. Dissertation, Brigham Young University, Dec. 2007.

Laiko, V. V., "Orthogonal Extraction Ion Mobility Spectrometry", Poster, Proceedings of the 54th ASMS Conference on Mass Spectrometry and Allied Topics, May 28-Jun. 1, Seattle, WA (2006).

* cited by examiner

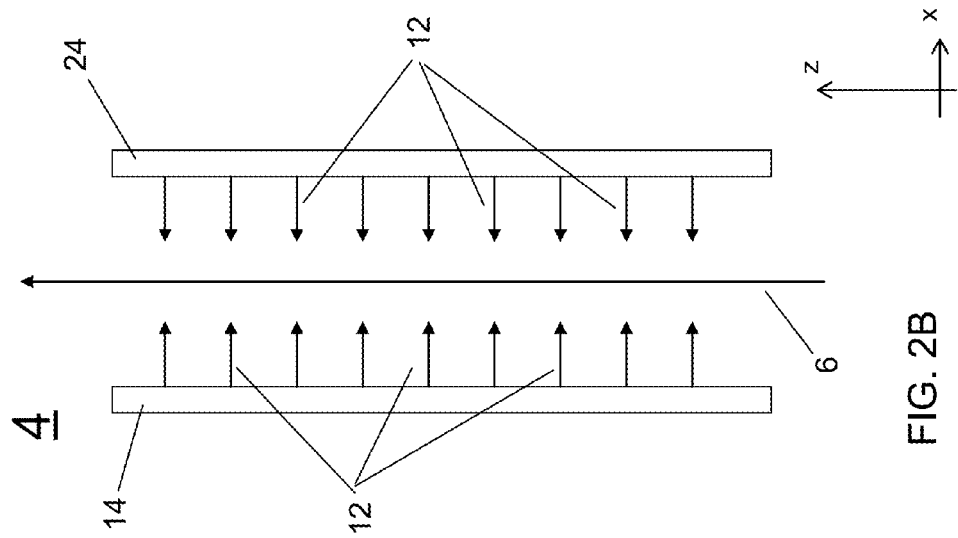
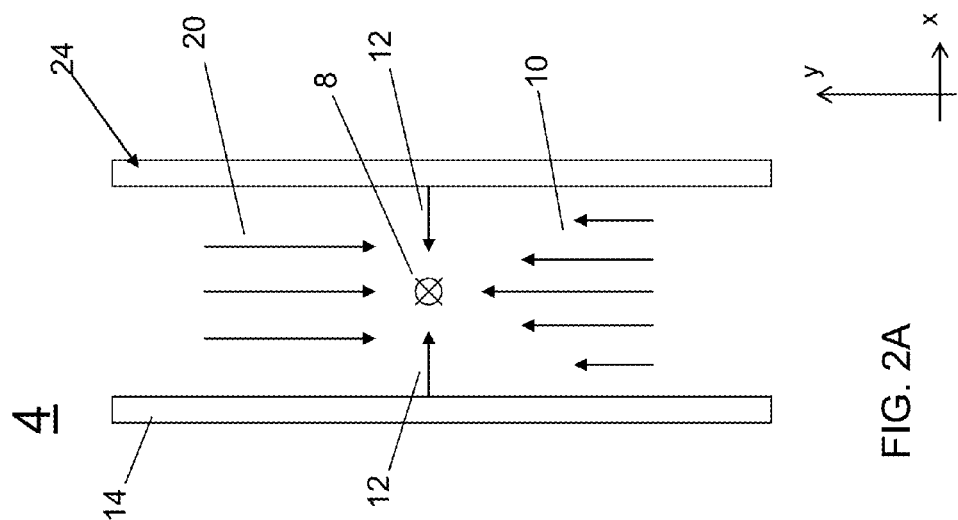

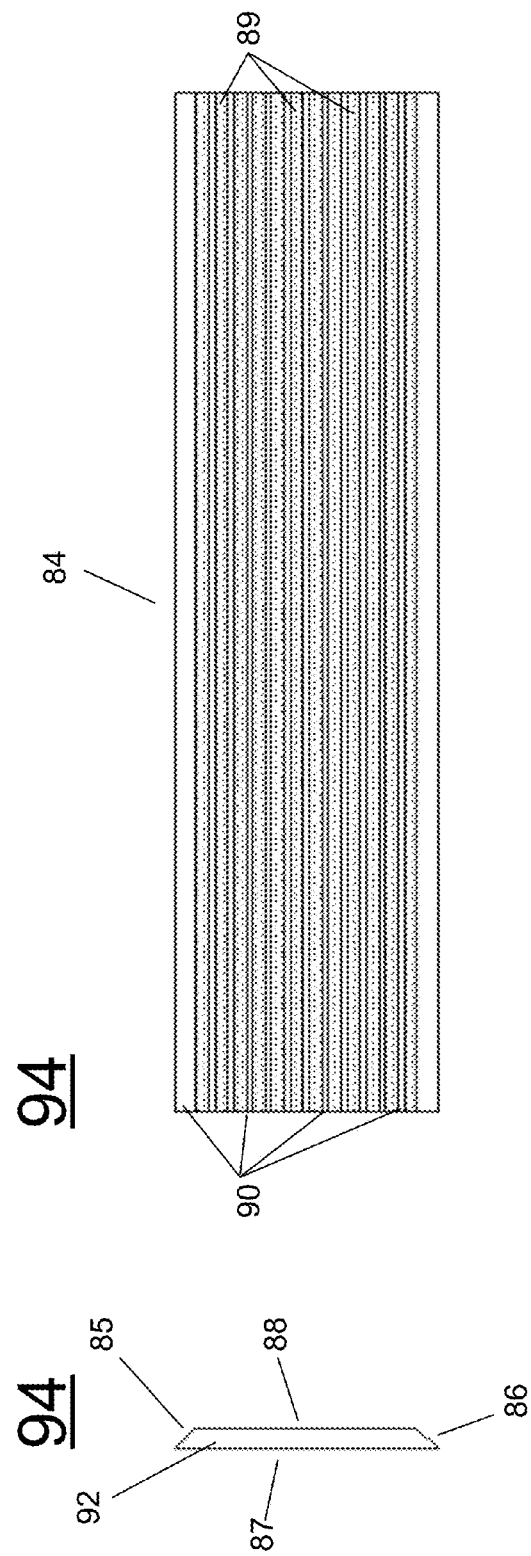

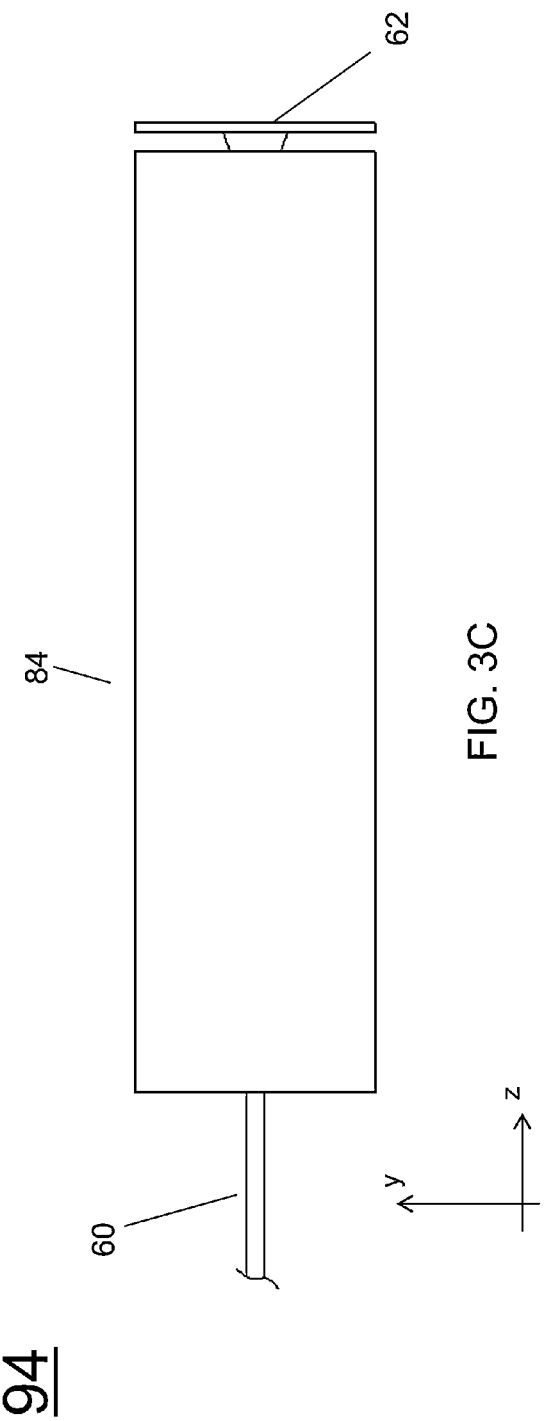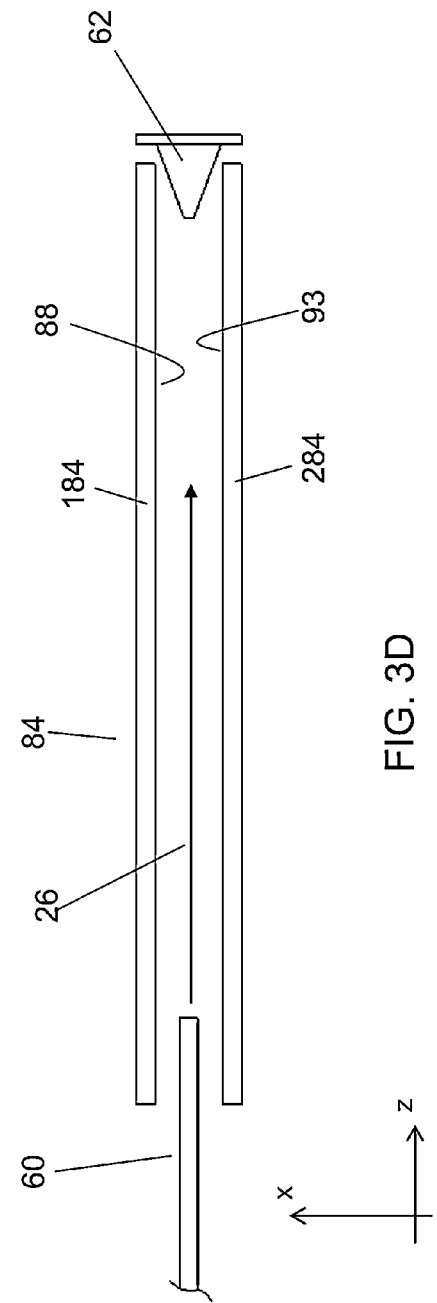

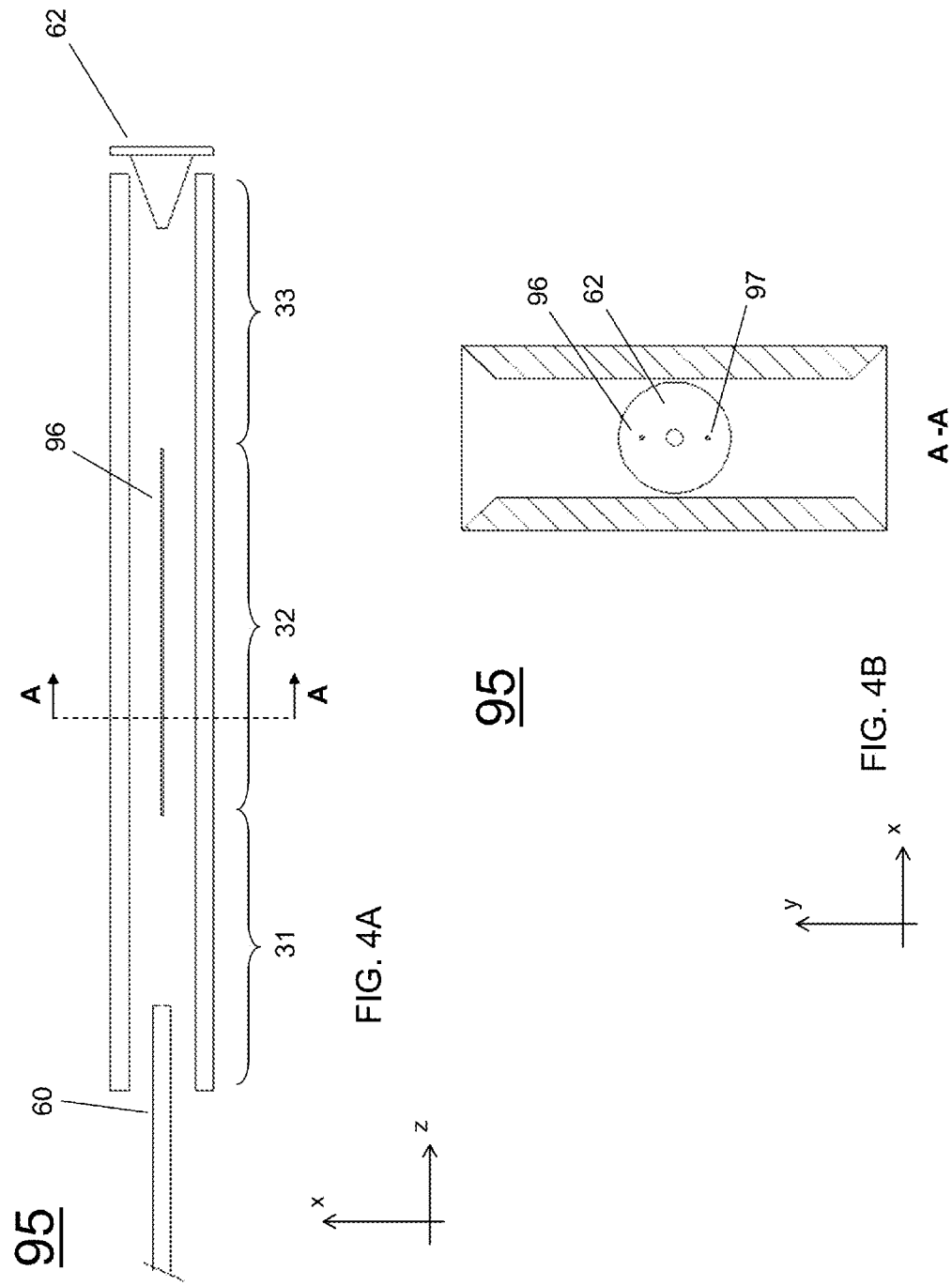

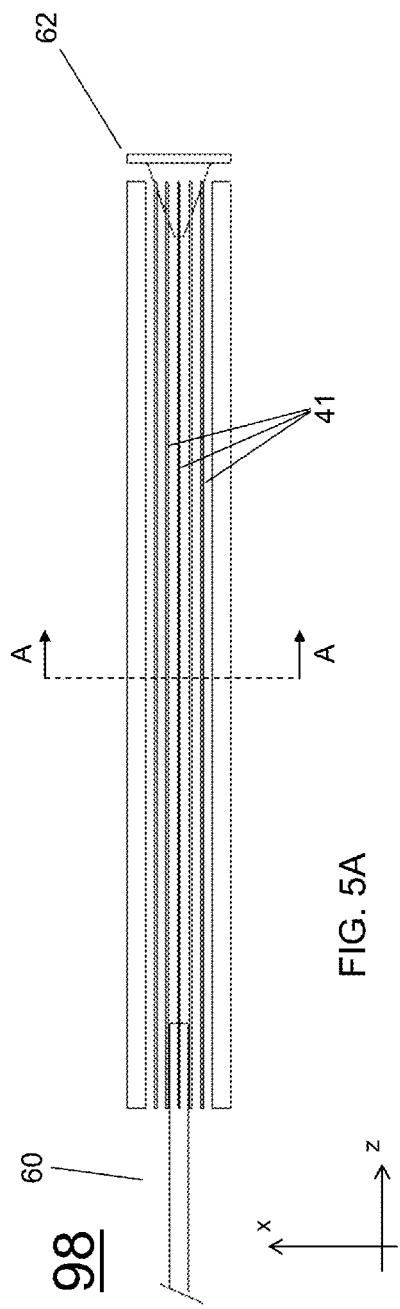
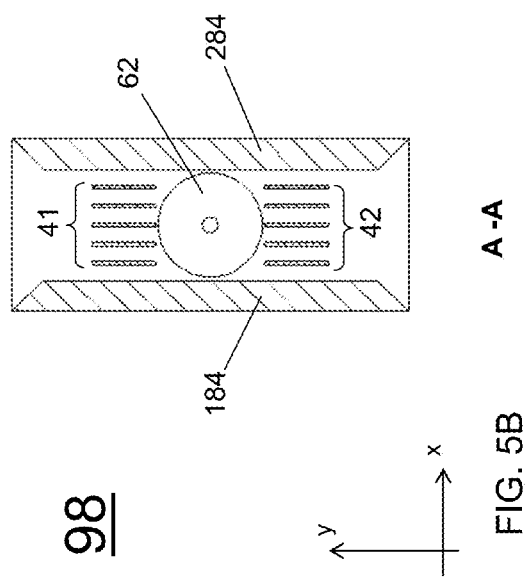
FIG. 5A
FIG. 5B

APPARATUS AND METHOD FOR CROSS-FLOW ION MOBILITY SPECTROMETRY

BACKGROUND

The present invention relates to methods for the analysis of samples by ion mobility and by ion mobility combined with mass spectrometry. The apparatus and methods for sample handling and analysis described herein are enhancements of the techniques referred to in the literature relating to mass spectrometry and ion mobility spectrometry—important tools in the analysis of a wide range of chemical compounds. Specifically, ion mobility spectrometers can be used to determine the cross section of analyte ions and mass spectrometers can be used to determine their molecular mass (more precisely the ratio of molecular mass to electric charge, hereafter referred to as mass). The analysis of samples by ion mobility spectrometry and mass spectrometry comprises three main steps—formation of gas phase ions from sample material, mobility and/or mass analysis of the ions to separate the ions from one another according to ion mobility and/or mass, and detection of the ions. A variety of means and methods exist in the fields of mass and mobility spectrometry to perform each of these three functions. The particular combination of the means and methods used in a given mobility or mass spectrometer determine the characteristics of that instrument.

To mass analyze ions, for example, one might use magnetic (B) or electrostatic (E) analysis, wherein ions passing through a magnetic or electrostatic field will follow a curved path. In a magnetic field, the curvature of the path will be indicative of the momentum-to-charge ratio of the ion. In an electrostatic field, the curvature of the path will be indicative of the energy-to-charge ratio of the ion. If magnetic and electrostatic analyzers are used consecutively, then both the momentum-to-charge and energy-to-charge ratios of the ions will be known and the mass of the ion will thereby be determined. Other well known mass analyzers are the quadrupole (Q), the ion cyclotron resonance (ICR), the time-of-flight (TOF), and the Paul ion trap analyzers. More recently, linear quadrupole ion traps [J. Schwartz, M. Senko, and J. Syka, J. Am. Soc. Mass Spectrom. 13, 659 (2002); J. Hager, Rapid Commun. Mass Spectrom. 16, 512 (2002)] have become more wide spread. A new analyzer, the orbitrap, based on the Kingdon trap [K. Kingdon, Phys. Rev. 21, 408 (1923)] was recently described by A. Makarov [Q. Hu et al., J Mass Spectrom. 40, 430 (2005)]. The analyzer used in conjunction with the means and method described here may be any of a variety of these.

Before mass analysis can begin, gas phase ions must be formed from a sample material. If the sample material is sufficiently volatile, ions may be formed by electron ionization (EI) or chemical ionization (CI) of the gas phase sample molecules. Alternatively, for solid samples (e.g., semiconductors, or crystallized materials), ions can be formed by desorption and ionization of sample molecules by bombardment with high energy particles. Further, Secondary Ion Mass Spectrometry (SIMS), for example, uses keV ions to desorb and ionize sample material. In the SIMS process a large amount of energy is deposited in the analyte molecules, resulting in the fragmentation of fragile molecules. This fragmentation is undesirable in that information regarding the original composition of the sample (e.g., the molecular weight of sample molecules) will be lost.

For more labile, fragile molecules, other ionization methods now exist. The plasma desorption (PD) technique was introduced by Macfarlane et al. (R. D. Macfarlane, R. P. Skowronski, D. F. Torgerson, Biochem. Biophys. Res Commun. 60 (1974) 616)("McFarlane"). Macfarlane discovered that the impact of high energy (MeV) ions on a surface, like SIMS would cause desorption and ionization of small analyte molecules. However, unlike SIMS, the PD process also results in the desorption of larger, more labile species (e.g., insulin and other protein molecules).

Additionally, lasers have been used in a similar manner to induce desorption of biological or other labile molecules. See, for example, Cotter et al. (R. B. VanBreeman, M. Snow, R. J. Cotter, Int. J. Mass Spectrom. Ion Phys. 49 (1983) 35; Tabet, J. C.; Cotter, R. J., Tabet, J.C., Anal. Chem. 56 (1984) 1662; or R. J. Cotter, P. Demirev, I. Lys, J. K. Olthoff, J. K.; Lys, I.: Demirev, P.: Cotter et al., R. J., Anal. Instrument. 16 (1987) 93). Cotter modified a CVC 2000 time-of-flight mass spectrometer for infrared laser desorption of non-volatile biomolecules, using a Tachisto (Needham, Mass.) model 215G pulsed carbon dioxide laser. The plasma or laser desorption and ionization of labile molecules relies on the deposition of little or no energy in the analyte molecules of interest.

The use of lasers to desorb and ionize labile molecules intact was enhanced by the introduction of matrix assisted laser desorption ionization (MALDI) (K. Tanaka, H. Waki, Y. Ido, S. Akita, Y. Yoshida, T. Yoshica, Rapid Commun. Mass Spectrom. 2 (1988) 151 and M. Karas, F. Hillenkamp, Anal. Chem. 60 (1988) 2299). In the MALDI process, an analyte is dissolved in a solid, organic matrix. Laser light of a wavelength that is absorbed by the solid matrix but not by the analyte is used to excite the sample. Thus, the matrix is excited directly by the laser, and the excited matrix sublimes into the gas phase carrying with it the analyte molecules. The analyte molecules are then ionized by proton, electron, or cation transfer from the matrix molecules to the analyte molecules. This process (i.e., MALDI) is typically used in conjunction with time-of-flight mass spectrometry (TOFMS) and can be used to measure the molecular weights of proteins in excess of 100,000 Daltons.

Atmospheric Pressure Ionization (API) includes a number of ion production means and methods. Typically, analyte ions are produced from liquid solution at atmospheric pressure. One of the more widely used methods, known as electrospray ionization (ESI), was first suggested for use with mass spectrometry by Dole et al. (M. Dole, L. L. Mack, R. L. Hines, R. C. Mobley, L. D. Ferguson, M. B. Alice, J. Chem. Phys. 49, 2240, 1968). In the electrospray technique, analyte is dissolved in a liquid solution and sprayed from a needle. The spray is induced by the application of a potential difference between the needle and a counter electrode. The spray results in the formation of fine, charged droplets of solution containing analyte molecules. In the gas phase, the solvent evaporates leaving behind charged, gas phase, analyte ions. This method allows for very large ions to be formed. Ions as large as 1 MDa have been detected by ESI in conjunction with mass spectrometry (ESMS).

In addition to ESI, many other ion production methods might be used at atmospheric or elevated pressure. For example, MALDI has recently been adapted by Laiko et al. to work at atmospheric pressure (Victor Laiko and Alma Burlingame, "Atmospheric Pressure Matrix Assisted Laser Desorption", U.S. Pat. No. 5,965,884, and Atmospheric Pressure Matrix Assisted Laser Desorption Ionization, poster #1121, 4th International Symposium on Mass Spectrometry in the Health and Life Sciences, San Francisco, Aug. 25-29, 1998) and by Standing et al. at elevated pressures (Time of Flight Mass Spectrometry of Biomolecules with Orthogonal Injection+Collisional Cooling, poster #1272, 4th International Symposium on Mass Spectrometry in the Health and Life Sciences, San Francisco, Aug. 25-29, 1998; and Orthogonal Injection TOFMS Anal. Chem. 71(13), 452A (1999)). The benefit of adapting ion sources in this manner is that the ion optics (i.e., the electrode structure and operation) in the mass analyzer and mass spectral results obtained are largely independent of the ion production method used.

The elevated pressure MALDI source disclosed by Standing differs from what is disclosed by Laiko et al. Specifically, Laiko et al. disclose a source intended to operate at substantially atmospheric pressure. In contrast, the source disclosed by Standing et al. is intended to operate at a pressure of about 70 mtorr.

More recently, Takats et al. [Z. Takats, J. M. Wiseman, B. Gologan, and R. G. Cooks, Science 306, 471 (2004)] introduced yet another atmospheric pressure ionization method known as desorption electrospray ionization (DESI). According to Takats et al., DESI is a method for producing ions from analyte on a surface. Electrosprayed charged droplets and ion of solvent are directed at the surface under study. The impact of the charged droplets on the surface results in the desorption and ionization of the analyte to form gas phase analyte ions.

Analyte ions produced via an API method need to be transported from the ionization region through regions of differing pressures and ultimately to a mass analyzer for subsequent analysis (e.g., via time-of-flight mass spectrometry (TOFMS), Fourier transform mass spectrometry (FTMS), etc.). In some prior art sources, this was accomplished through use of a small orifice between the ionization region and the vacuum region. In other prior art, dielectric capillaries have been used to transmit ions entrained in a carrier gas from a high pressure ion production region into the vacuum chamber of mass spectrometers—see, for example, Fenn et al., U.S. Pat. No. 4,542,293 and Whitehouse et al., U.S. Pat. No. 5,844,237. In U.S. Pat. No. 6,777,672, incorporated herein by reference, Park describes a multiple section capillary for interfacing various ion production means and for transporting ions into the vacuum chamber of a mass spectrometer.

Importantly, ions are carried through the transfer capillary by entrainment in gas which is pumped from the ion production region, through the capillary, into the first vacuum region of the mass spectrometer. Typically, the gas pressure at the capillary inlet is about one atmosphere whereas the pressure at the capillary outlet, into the first pumping region, is between one and three millibar. Under these conditions, the velocity of the gas in the capillary is about 100 m/s. It is the "force" associated with this high velocity gas that is able to drive the ions away from the electrically attractive potential at the capillary entrance and towards the electrically repulsive potential at the capillary exit.

Once through the capillary, analyte ions are guided by a combination of gas flows and electric fields through differential pumping regions to a mobility and/or mass analyzer. There the ions are analyzed and detected so as to yield mobility and/or mass spectra. Any known mass or mobility analyzer or combination of mass or mobility analyzers including time-of-flight, quadrupole, Paul trap, linear ion trap, orbitrap, electric or magnetic sector, ion cyclotron resonance analyzers, drift cell, differential mobility analyzer, or trapped ion mobility analyzer might be used.

In co-pending application Ser. No. 13/152,363, incorporated herein by reference, the present inventor discloses an abridged RF quadrupole for the transport and mass analysis of ions. The abridged RF quadrupole design comprises a multitude of electrode structures arranged rectilinearly and symmetrically about a central axis (designated the z-axis). Voltages are applied to the electrode structures generating an electric field inside the abridged RF quadrupole having the form:

$$\Phi(x, y, t) = \frac{-\Phi_o(t) \cdot x \cdot y}{2r_o^2} + E_x(t) \cdot x + E_y(t) \cdot y + c \qquad (1)$$

where $\Phi$ is the electric field potential, $E_x$ and $E_y$ are functions of time relating to a homogeneous dipole field, $c$ and $r_o$ are constants, and x and y are coordinates. $\Phi_0$ may be any function of time, t, however, as an example, is given by:

$$\Phi_0(t) = V\sin(2\pi f t) + U, \qquad (2)$$

where V and U are RF and DC potentials respectively. Thus, in accordance with equation (1), the abridged RF quadrupole can support an RF quadrupole field which tends to focus ions to an axis—i.e. the z-axis—and a dipole field which can be used to excite ions or otherwise apply a force to the ions orthogonal to the z-axis.

The "mobility" of analyte ions through a gas can be measured under the influence of a static uniform electric field (drift type IMS). Such ion mobility spectrometers are described in detail in the literature [see, for example, G. Eiceman and Z. Karpas, Ion Mobility Spectrometry (CRC. Boca Raton, Fla. 1994); and Plasma Chromatography, edited by T. W. Carr (Plenum, New York, 1984)]. At low electric field strengths—e.g. a few kilovolts per cm—the speed of analyte ions through a gas is measured. To start the measurement, ions are pulsed into the entrance of the mobility analyzer. In the mobility analyzer, a uniform electric field accelerates the ions towards the end of the analyzer. Collisions with gas in the analyzer tend to dampen the ion motion. The action of the electric field and collision of ions with the gas thus results in an average ion speed through the gas. At the far end of the analyzer, the ions strike a detector and are detected. By measuring the time between the introduction of ions into the analyzer and the detection of the ions, the speed of the ions, and therefore their mobility, can be determined.

At low field strengths, the mobility of an ion is a constant relating the speed of the ion to the strength of the electric field. However, at high electric field strengths, the mobility of the ions varies with electric field strength. This gives rise to field asymmetric ion mobility spectrometry (FAIMS)—an extension of IMS which takes advantage of the change in ion mobility at high field strengths. FAIMS is described in detail in the literature [I. Buryakov, E. Krylov, E. Nazarov, and U. Rasulev, Int. J. Mass Spectrom. Ion Phys. 128. 143 (1993); D. Riegner, C. Harden, B. Carnahan, and S. Day, Proceedings of the 45th ASMS Conference on Mass Spectrometry and Allied Topics, Palm Springs, Calif., Jun. 1-4, 1997, p. 473; B. Carnahan, S. Day, V. Kouznetsov, M. Matyjaszczyk, and A. Tarassov, Proceedings of the 41st ISA Analysis Division Symposium, Framingham, Mass., Apr. 21-24, 1996, p. 85; and B. Carnahan and A. Tarassov, U.S. Pat. No. 5,420,424].

In recent years, IMS and FAIMS spectrometers have been combined with mass spectrometry. In U.S. Pat. No. 5,905,258 Clemmer and Reilly combine IMS with a time of flight mass spectrometer (TOFMS). This provides for a first analysis of the ions by IMS followed by a second analysis via TOFMS. Ultimately, this yields a two dimensional plot containing both the mobility and mass of the ions under investigation. The advantages of this type of combined analyzer over a mass spectrometer alone are described in detail in the literature [C. S. Srebalus et al., Anal. Chem. 71(18), 3918 (1999); J. A. Taraszka et al., J. Proteom. Res. 4, 1223 (2005); R. L. Wong, E. R. Williams, A. E. Counterman, and D. Clemmer, J. Am.

Soc. Mass Spectrom. 16, 1009 (2005)] and include the separation of chemical background from analyte species for an improved signal-to-noise ratio (S/N), and the separation of ions based on compound class or charge state for easier mass spectral interpretation.

Similarly, in U.S. Pat. No. 6,504,149, for example, Guevremont et al. combine a FAIMS device with a mass spectrometer. As detailed in the literature, a combined FAIMS mass spectrometer has similar advantages as an IMS mass spectrometer [A. Shvartsburg, K. Tang, R. Smith, J. Am. Soc. Mass Spectrom. 16, 2 (2005); D. A. Barnett, B. Ells, R. Guevremont, and R. W. Purves, J. Am. Soc. Mass Spectrom. 13, 1282 (2002)]. For example, a combined FAIMS mass spectrometer has an improved signal-to-noise ratio over a mass spectrometer alone because the FAIMS device can filter away the chemical background.

Several other methods of IMS separation have been demonstrated in the prior art. For example, J. Zeleny described a parallel flow ion mobility analyzer in "J. Zeleny, Philos. Mag. 46, 120(1898)." In Zeleny's instrument, a voltage V is applied between two parallel grids separated by a distance h. Gas and ions flow through the grids parallel to the electric field. The electric field retards the motion of the ions such that the average velocity of ions between the grids is $v=E \cdot K-u$, where E is the electric field strength, K is the ion mobility and u is the air flow velocity. The mobility of the ions can be calculated as $K=h/Et+u/E$.

In U.S. Pat. No. 5,847,386, incorporated in its entirety herein by reference, Thompson and Jolliffe suggest an ion mobility method wherein "ions are admitted into an RF multipole with an axial field, in the presence of cooling gas or drift gas, the ion velocity will reach a constant value which is proportional to the axial field. Ions of different size will drift at different velocities dependant on their shape, mass and charge, and be separated in time when they reach the exit of the device. If the exit gate . . . is opened at an appropriate time, only ions of a certain type will be admitted in the following analyzing device or other detector such as a mass spectrometer. This mobility separation may be applied to assist in the analysis of a mixture of ions . . . "

Also recently Page et al. [J. S. Page et al., J. Mass Spectrom. 40, 1215 (2005)] and Loboda et al. [U.S. Pat. No. 6,630,662 incorporated herein in its entirety by reference] employed the parallel flow analyzer method of Zeleny in combination with RF ion optical devices. However, the method of Page et al. results in a non-uniform gas flow—i.e. the flow direction and speed is dependent on both the axial and radial position within the device. Also the DC axial electric field is non-uniform and includes radial components. Furthermore, the RF confining field generated in the Page device includes an axial component. This tends to interfere with the mobility separation and introduces a mass effect to the separation. That is, the RF field has a greater effect on ions of a given mass range and a lesser effect on ions of another. Finally, in the method of Page et al. ions of a selected mobility cannot actually be isolated from ions of greater and lesser mobility. Rather, ions of high mobility are eliminated from a stream of ions having both high and low mobility. Similarly, Loboda does not teach a means and method whereby ions from a continuous ion source can be effectively introduced into an RF device for mobility analysis.

In U.S. Pat. No. 7,838,826 B1 (M. A. Park, 2008) and in co-pending application Ser. Nos. 13/094,102, 13/094,128, and 13/094,146, ion mobility spectrometers are presented, the size of which amounts to about ten centimeters only. It is based upon moving gases driving ions over an electric counter-field barrier in a modified ion funnel built into a time-of-flight mass spectrometer. Thus, this instrument essentially roots back to J. Zeleny cited above. Unlike these many other trials to build small ion mobility spectrometers, the device by M. A. Park has already achieved ion mobility resolutions in excess of 100, and even considerably higher resolutions can be expected by future improvements.

Yet another prior art method of mobility analysis is known as differential mobility analysis (DMA). An example of such an analyzer was described by Tammet (Tammet, H. "The limits of air ion mobility resolution." Proc. 11th Int. Conf. Atmos. Electr., NASA, MSFC, Alabama, pp 626-629 (1999).) as using the "method of inclined grids". As described by Tammet, "The orientation of the electric field in the analyzer is . . . not perpendicular to the air flow as assumed in traditional mobility analyzers . . . . As distinct from the Zeleny grid instrument, [the analyzer of Tammet] has inlet and outlet slits for ions like traditional DMA-s. The ions to be separated do not pass through the grids and there is no harmful effect of adsorption of ions on the grids . . . . An essential advantage of the method is that the grids suppress the turbulence and maintain the plug flow profile." Furthermore, Tammet claims the method provides improved resolution over traditional mobility analyzers.

In a similar vein, N. Agbonkonkon [N. Agbonkonkon, Counter-flow Ion Mobility Analysis Design, Instrumentation, and Characterization, Ph.D. Dissertation, Brigham Young University, December 2007] suggested the method of "counter-flow ion mobility analysis" (CIMA). According to Agbonkonkon " . . . a high electric field (over 2500 V/cm) and high counter-gas velocity (over 10 m s-1) provide opposing forces to stop the motion of the [selected mobility] ions in space. A third force, which is stronger than either of the opposing forces is used to quickly move the ions to the detector. This third force is orthogonal to both the opposing electric field and gas flow." In one embodiment according to Agbonkonkon, shown in FIG. 1, sample ions are passed between two perforated cylinders. The force on ions due to gas flowing from the inner cylinder to the outer cylinder is counteracted by an electric field between the cylinders.

Of the above cited prior art mobility analyzers, only DMA and CIMA are able to filter ions according to their mobility. That is, DMA and CIMA can provide a continuous ion beam of a selected mobility. However, the DMA and CIMA analyzers described in the prior art transmit ions only inefficiently because there is no mechanism to actively retain selected ions. Also, the prior art Zeleny and Agbonkonkon devices suffer from having substantially non-uniform gas velocities, resulting in poor ion mobility resolutions. Furthermore, it is not possible to operate these prior art devices in such a manner that ions are transmitted through the devices without mobility analysis—i.e. transmitting ions of all mobilities through the devices. It is therefore part of the purpose of the present invention to provide a device and method whereby ions can be mobility filtered and efficiently transmitted through the device. Another purpose of the present invention is to provide a device wherein the ions are separated according to their mobility with high resolution using guided gas flows with non-uniform gas velocity. It is a further purpose to provide a device and method whereby ions can be either mobility filtered and transmitted or efficiently transmitted without mobility filtering. Other shortcomings in prior art devices described above limit their mobility resolution, the sensitivity of the instruments employing them—i.e. many ions of interest are lost due to poor efficiency in the mobility device—and the accuracy of the mobility determinations. It is, in part, the purpose of the present invention to overcome these prior art limitations.

SUMMARY

The present invention provides IMS devices and methods which improve mobility resolution and accuracy of ion mobility determination over prior art CIMA and DMA. The IMS devices according to the present invention can be combined with mass spectrometers to produce tandem ion mobility-mass spectrometer (IMS/MS) instruments.

In a first aspect, an IMS device comprises means for generating a first and second electric field in a volume wherein the first electric field confines ions to a longitudinal axis along at least one direction orthogonal to the said axis and wherein the second electric field is a DC field orthogonal to the longitudinal axis; and a duct forming a path of a gas flow in the volume, the gas flow having a velocity component orthogonal to the longitudinal axis, wherein the DC field is counteracting the orthogonal velocity component of the gas flow.

The analytical direction of the IMS device (cross-flow mobility analyzer) is defined by the orthogonal velocity component of the gas flow and the above mentioned DC field (DC analytical field). Ions introduced into the volume on the longitudinal axis experience two counteracting forces along the analytical direction: a "drag force" due to the gas flow and a force due to the DC analytical field. The two forces are balanced only for ions having a predetermined mobility such that only these ions will follow a path centered on the longitudinal axis whereas other ion species are displaced from the longitudinal axis due to the unbalanced forces and are thereby lost. Ions with different mobility are spatially separated along the analytical direction.

The cross-flow IMS device is preferably used as filter-type analyzer. Thus, for example, when a multicomponent continuous beam of ions is introduced at the inlet of the cross-flow mobility analyzer, a continuous beam of selected ions with predetermined mobility will be produced at its exit. By scanning the field strength of the DC analytical field, the mobility of the transmitted ions can be scanned. Recording the intensity of the ions leaving the volume on the longitudinal axis while scanning the field strength of the DC analytical field will yield an ion mobility spectrum. However, other parameters can be adjusted and scanned for recording an ion mobility spectrum, for example the velocity component orthogonal to the longitudinal axis, the gas pressure of the gas and/or the temperature of the gas.

The duct forming the path of the gas flow is preferably oriented orthogonally to the longitudinal axis such that the axis of the duct is equal to the analytical direction. The inner volume of the duct can substantially be the volume in which the first and second fields are generated. However, the inner volume of the duct can also be smaller or greater than the volume. The duct can be positioned between two gas reservoirs at different pressure or can be part of a wind tunnel in order to generate the gas flow in the duct. The duct may be a cylinder which has an entrance and exit opening for the gas flow, each opening located at an opposite side of the longitudinal axis, and which is laterally closed along the path of the gas flow except for an ion inlet and ion outlet where the longitudinal axis intersects with the cylinder. The cylinder can have an arbitrary cross section, e.g. rectangular or elliptical. The cylinder can be right or sloped with regard to the basis. The cross section of a laterally closed duct (also referred to as a cylinder in here) can also vary in size and shape along the axis of the duct.

In a first embodiment of a cylindrical duct, the orthogonal velocity component of the gas flow and the second electric field are substantially constant along the longitudinal axis. This can be achieved by one of an ion inlet/outlet located in the plug flow region at the entrance opening or at a recess of the cylinder, structural elements positioned inside the cylinder disturbing the parabolic velocity profile within the cylinder, and a cross section of the cylinder which widens along the axis of the duct.

In a second embodiment of a cylindrical duct, the orthogonal velocity component of the gas flow has a non-uniform profile along the longitudinal axis, in particular a parabolic velocity profile. The counteracting DC analytical field can be adapted to have a non-uniform field strength profile along the longitudinal axis to compensate the inhomogeneous velocity profile.

The duct can comprise one or more extended lateral openings along the path of the gas flow at a side where ions are introduced into the volume or are leaving the volume, respectively. Gas may be introduced at the lateral openings to generate a plug flow with a substantially constant orthogonal velocity component along the longitudinal axis. Lateral opening along the duct axis may further inhibit the development of a parabolic velocity profile in the direction of the longitudinal axis. For example, the duct can be formed by two parallel plates positioned about the longitudinal axis so that the path of the gas flow is oriented parallel to the surface of said plates and the ion path is positioned symmetrically between the plates. The counteracting DC field can be adapted to have spatially varying field strength along the longitudinal axis to compensate a remaining inhomogeneity of the orthogonal velocity component on the longitudinal axis.

The IMS device may be used in conjunction with any known ion production method including laser desorption (LD), matrix assisted laser desorption ionization (MALDI), electrospray ionization (ESI), chemical ionization (CI), photoionization (PI), or any other known method of producing ions.

The means for generating the electric fields can comprise a set of RF/DC electrodes connected to an RF voltage supply and to a DC voltage supply wherein the first electric field is an electric RF field which radially confines the ions to the longitudinal axis. Radial confinement means that a pseudopotential force is acting on the ions along two linear independent directions orthogonal to the longitudinal axis.

The set of RF/DC electrodes may be arranged as an abridged RF quadrupole about the longitudinal axis, generating an electric field inside the volume having the form:

$$\Phi(x, y, t) = \frac{\Phi_o(t) \cdot x \cdot y}{2r_o^2} + E_x(t) \cdot x + E_y(t) \cdot y,$$

where $\Phi_o(t)$ is an RF potential, $E_x(t)$ and $E_y(t)$ are functions of time relating to an adjustable DC field, $r_o$ is a constant, and x and y are orthogonal coordinates. The duct comprises two parallel plates positioned symmetrically about the longitudinal axis and defining the volume between them. The path for the analytical gas flow is oriented parallel to the surface of the plates and having a component orthogonal to the longitudinal axis. The volume comprises an ion inlet and an ion outlet centered on longitudinal axis. The pseudopotential force resulting from said RF confining field is normal to the surface of the plates and directed into the volume.

The means for generating the electric fields can otherwise comprise a set of DC electrodes connected to a DC voltage supply wherein the first electric field is an electric DC field confining the ions only along one orthogonal direction to the longitudinal axis. The confining direction is orthogonal to the second electric DC field (DC analytical field), i.e. to the analytical direction. The set of DC electrodes may be arranged and/or applied with DC potentials to generate an electric field inside the volume having the form:

$$\Phi(x, y, z, t) = \frac{\Phi_0(x^2 - y^2)}{r_o^2} + E_y(t) \cdot y$$

where $\Phi_0$ is a DC potential, $E_y(t)$ is a function of time relating to an adjustable DC analytical field, $r_o$ is a constant, and x and y are orthogonal coordinates, and z is the coordinate along the longitudinal axis. The analytical direction is along the y-coordinate. Ions are not confined along the analytical direction. Selected ions of a predetermined mobility do not experience a dragging force along the analytical direction, but stay centered on the longitudinal axis. Other ions species experience a dragging force and are therefore deflected from the longitudinal axis and may even exit the volume along the analytical direction because of the missing confinement along the analytical direction. Selected ions are also not confined along the analytical direction, but they only experience diffusion along the analytical direction, i.e. the spatial distribution of selected ions broadens along the analytical axis while moving through the volume.

The set of RF/DC electrodes and the DC electrodes can be supported on plates or curved surfaces forming the duct. The electrodes can be formed of electrically conducting and/or resistive deposits on the plates or curved surfaces. However, the electrodes do not need to be integrated in the duct, but can be separated from it.

The IMS device can further comprise entrance, analytical, and exit regions. The entrance region may comprise a capillary by which ions are introduced into the volume. The exit region may comprise a skimmer by which ions (centered on or displaced from the longitudinal axis) may be extracted from the volume. The IMS device, in particular those utilizing a confining RF field like the abridged RF quadrupole, may further comprise filtering electrodes placed parallel to and on opposite sides of the longitudinal axis. The filtering electrodes preferably extend along the analytical region and are used to neutralize ions which are displaced from the longitudinal axis. The filtering electrodes can be wires or conducting foils which are preferably located on zero potential lines or planes.

The IMS device can further comprise means for driving ions along the longitudinal axis through the volume, e.g. by the gas flow having an additional velocity component along the longitudinal axis, by an axial electric DC, by an axial electric RF field and/or by accelerating the ions in direction of the longitudinal prior to introducing them into the volume.

In a second aspect, an ion mobility-mass spectrometer (IMS/MS) system comprises an ion source; a cross-flow mobility analyzer comprising means for generating a first and second electric field in a volume wherein the first electric field confines ions to a longitudinal axis along at least one direction orthogonal to the said axis and wherein the second electric field is a DC field orthogonal to the longitudinal axis; and a duct forming a path of a gas flow in the volume, the gas flow having a velocity component orthogonal to the longitudinal axis, wherein the DC field is counteracting the orthogonal velocity component of the gas flow; and a mass analyzer.

The ion source can be selected from the group comprising laser desorption (LD), matrix assisted laser desorption ionization (MALDI), electrospray ionization (ESI), chemical ionization (CI), and photoionization (PI).IMS/MS system may comprise at least one of following types of ion sources: laser desorption (LD), matrix assisted laser desorption ionization (MALDI), electrospray ionization (ESI), chemical ionization (CI), and photoionization (PI).

The mass analyzer can be one of time-of-flight analyzer, quadrupole filter, RF-ion trap (like Paul trap or linear ion trap), electrostatic trap (like the Orbitrap), electric or magnetic sector, and ion cyclotron resonance analyzer. The IMS/MS system can comprise more than one mass analyzer, for example two quadrupole filters or a quadrupole filter combined with a high resolving mass analyzer (like an orthogonal time of flight mass analyzer or ion cyclotron resonance analyzer) wherein the cross-flow analyzer is positioned between both mass analyzers. The cross flow analyzer may also be positioned between the ions source and a first mass analyzer of the IMS/MS system.

In a third aspect, a method for mobility analyzing ions comprises: (a) generating a first electric field in a volume, the first electric field confining ions along a longitudinal axis in the volume; (b) generating a second electric field in the volume, the second electric field being a DC field orthogonal to the longitudinal axis; generating a guided gas flow in the volume, the gas flow having a velocity component orthogonal to the longitudinal axis and counteracting the second electric field; (d) introducing ions on the longitudinal axis into the volume; and (e) detecting ions exiting the volume without being substantially displaced from the longitudinal axis.

The ions are introduced into the volume at an ion inlet centered on the longitudinal axis. Along the analytical direction, the ions experience two counteracting forces: the friction force of the orthogonal component of the gas flow and the counteracting DC analytical field. Selected ions are able to follow a stable path along the longitudinal axis towards the outlet of the cross-flow mobility analyzer because both forces are balanced for these ions. Other ions with different mobility experience a drag force and are therefore deflected from the longitudinal axis. Ions are spatially separated along the analytical direction according to their mobility. When ions are continuously introduced into the volume, a continuous beam of ions of the selected mobility will be produced at the outlet. Preferably, ions exiting the volume without being substantially displaced from the longitudinal axis are detected. However, ions displaced from the longitudinal axis and separated from other can also be selected and detected.

The following analytical parameters can be adjusted to select the mobility of ions exiting the volume, preferably without being displaced from the longitudinal axis: the field strength of the second electric field (DC analytical field), the orthogonal velocity component of the gas flow, the pressure of the gas flow and/or the temperature of the gas flow. By scanning one or more of these analytical parameters, the mobility of ions exiting the volume can be scanned. The ion signal of selected ions can be detected as a function of the scanned parameter so as to produce an ion mobility spectrum. Detection of ions can also comprise transferring the selected ions to a mass analyzer and analyzing the transferred ions according to their mass. Recording a series of mass spectra from ions selected according to mobility while scanning an analytical parameter will result in a combined ion mobility—mass spectrum.

The method can further comprise driving the ions through the volume along the longitudinal axis by one of the gas flow having an additional velocity component along the longitudinal axis, an axial electric DC, an axial electric RF field, and accelerating the ions in the direction of the longitudinal prior to introducing them into the volume.

The first electric field can be an RF field which radially confines the ions along the longitudinal axis, i.e. the ions experience a pseudopotential force acting along two linear independent directions orthogonal to the longitudinal axis. The confining RF field and the DC analytical field may be generated by an abridged quadrupole, the electric fields having the form:

$$\Phi(x, y, t) = \frac{\Phi_o(t) \cdot x \cdot y}{2r_o^2} + E_x(t) \cdot x + E_y(t) \cdot y$$

where $\Phi_o(t)$ is given by $V \cdot \sin(\omega \cdot t) + U$ (where V and U are RF and DC potentials respectively), $E_x(t)$ and $E_y(t)$ are functions of time relating to the adjustable DC field, $r_o$ is a constant, and x and y are orthogonal coordinates.

According to this embodiment, there are three modes of operation—"transmission", "mass analysis", and "mobility analysis" modes. In transmission mode, the abridged quadrupole is operated with a quadrupolar RF confining field but no DC analytical field or analytical gas flow. Inasmuch as there is only an RF field that radially confines ions, ions of a wide range of masses may pass unhindered from an inlet to an exit outlet along the longitudinal axis. In transmission mode, the range of masses which are transmitted can be tuned via the strength of the RF field as is well known from the prior. In mass analysis mode, ions are selected according to mass by adding a DC bias, U, to the quadrupolar field. This sort of mass selective stability is also known from the prior art. Using a quadrupolar RF field of a predetermined RF amplitude, V, and frequency, ω, and by applying a DC bias, U, of a predetermined magnitude, ions of only a selected mass or mass range will be transmitted from the inlet to the outlet. In mobility analysis mode, DC bias, U, is set to zero volts, an analytical gas flow is established, and a DC analytical field is applied counteracting the gas flow. The friction force induced by the analytical gas flow on ions of the selected mobility is counteracted by the DC analytical field. Providing an analytical gas flow of known velocity and a DC analytical field of known strength defines the mobility ions must have in order to stably move through the analyzer. Scanning the DC analytical field strength will similarly scan the mobility of the ions that are transmitted through the analyzer. Ions of lower or higher mobility will be deflected and lost. The RF field tends to prevent the ions from moving towards or colliding with electrodes of the abridged quadruple but does not significantly hinder the motion of the ions along the longitudinal axis.

The first electric field can otherwise be a DC field which confines ions along the longitudinal axis only in one direction orthogonal to the longitudinal axis and orthogonal to the direction of the second electric field.

Beside of the analytical parameters, other parameter of the cross flow analyzer may be adjusted while scanning one or more analytical parameters or may be optimized for transmitting ions of predetermined mobility through the volume. For example, the strength and/or frequency of the confining RF field may be adjusted with the field strength of the DC analytical field. By increasing the RF field strength with the field strength of the DC analytical field, one may improve the transmission of the low mobility ions that are transmitted at higher analytical field strengths. When used in a combination with a quadrupole filter, one might link the mass of the ions transmitted by the quadrupole mass filter with DC analytical field strength. That is, at higher analytical field strengths (transmitting lower mobility ions) one might transmit higher mass species through the quadrupole mass filter.

The prior art Zeleny and Agbonkonkon devices suffer from having substantially non-uniform gas velocities when gas is guided in a duct, resulting in poor ion mobility resolutions. The present invention provides cross-flow analyzers with improved performance by reducing the effect of non-uniform gas velocity. The ions are generally confined along an axis and thus to a region of the gas flow path which is spatially limited such that the variation of gas velocity within said region is reduced compared to the variation across the whole cross section of the gas path. In the case of a parabolic velocity profile, ions are preferably confined to the apex region where the velocity changes least. A variation of the gas velocity along the longitudinal axis can be further reduced by generating a plug flow at the axis, for example by structural flow elements inside the duct, lateral openings for an additional gas inflow, lateral openings or widening of the duct to inhibit the formation of a parabolic profile, positioning the ion path at the plug flow region or at a recess of the duct. A non-uniform gas velocity along the axis can also be compensated by adapting the field strength of the DC analytical field along the longitudinal axis to compensate, by generating the DC analytical field only in a limited region along the longitudinal axis and/or by introducing/extracting ions only in a limited region along the longitudinal axis, e.g. near the apex region of a parabolic velocity profile.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which:

FIG. 2A depicts an end view of a "cross-flow mobility analyzer" according to the present invention;

FIG. 2B depicts a top view of a "cross-flow mobility analyzer" according to the present invention;

FIG. 3A depicts an end view of an electrode structure of an abridged quadrupole as used in a cross-flow mobility analyzer according to the present invention;

FIG. 3B depicts a side view of an electrode structure of an abridged quadrupole as used in a cross-flow mobility analyzer according to the present invention;

FIG. 3C is a side view of a cross-flow mobility analyzer according to the present invention, incorporating an abridged quadrupole;

FIG. 3D is a bottom view of a cross-flow mobility analyzer according to the present invention, incorporating an abridged quadrupole;

FIG. 4A depicts a top view of a cross-flow mobility analyzer according to the present invention including wires for the elimination of deviant ions;

FIG. 4B depicts a cross-sectional view of a cross-flow mobility analyzer according to the present invention including wires for the elimination of deviant ions;

FIG. 5A depicts a top view of a cross-flow mobility analyzer according to the present invention including foil electrodes for forming a plug flow;

FIG. 5B depicts a cross-sectional view of a cross-flow mobility analyzer according to the present invention including foil electrodes for forming a plug flow;

DETAILED DESCRIPTION

Figure 1:
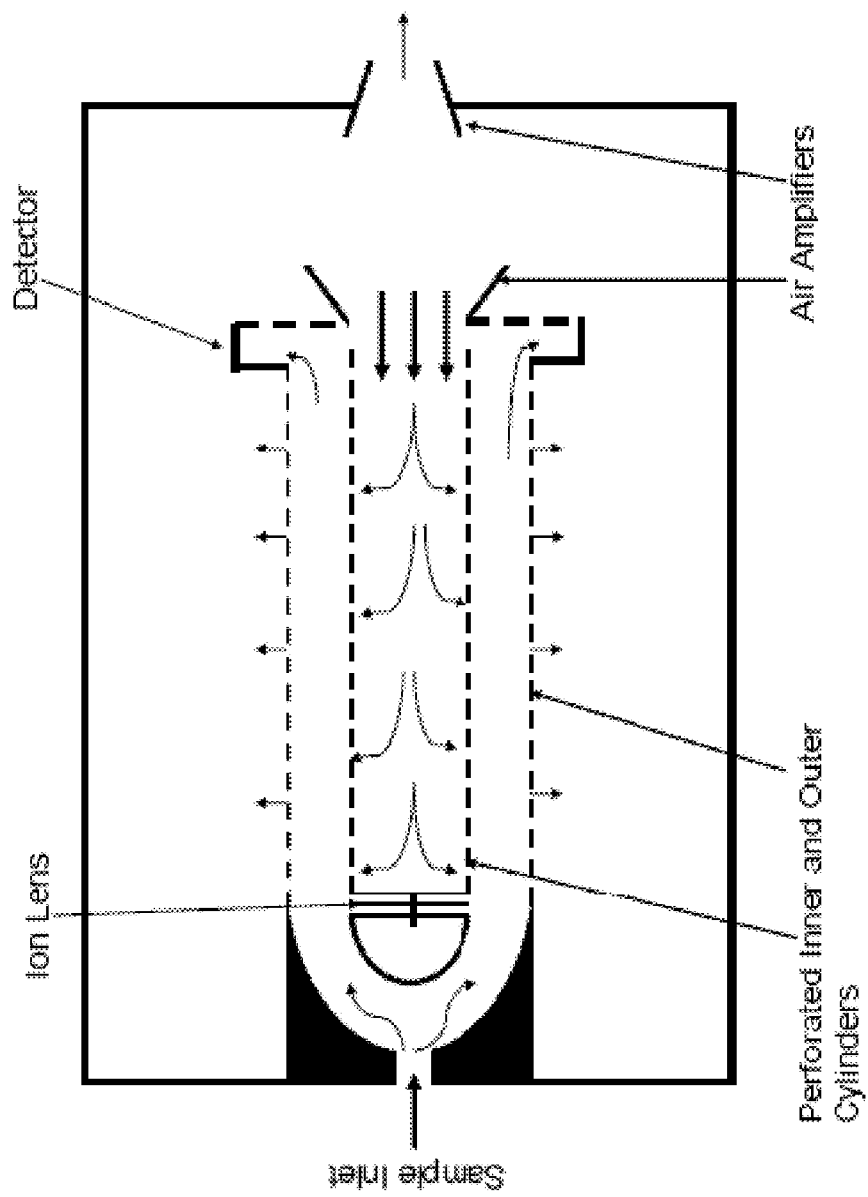
FIG. 1 is a depiction of a prior art CIMA analyzer according to Agbonkonkon.

As required, a detailed illustrative embodiment of the present invention is disclosed herein. However, techniques, systems and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

The following presents a detailed description of a preferred embodiment of the present invention, as well as some alternate embodiments of the invention. As discussed above, the present invention relates generally to the mobility and mass spectroscopic analysis of chemical samples and more particularly to mobility spectrometry combined to mass spectrometry. Specifically, a system and method are described for the tandem IMS/MS analysis of a sample. Reference is herein made to the figures, wherein the numerals representing particular parts are consistently used throughout the figures and accompanying discussion.

FIGS. 2A and 2B show depictions of the preferred embodiment of the present invention. FIG. 2A is an end view—i.e. along the z-axis—and FIG. 2B is a top view—along the y-axis—of cross-flow mobility analyzer 4 according to the present invention. As such a coordinate system is defined in FIGS. 2A and 2B. The system is defined such that in FIG. 2A, the x-axis is pointing right, the y-axis to the top and the z-axis into the page. Between FIG. 2A and FIG. 2B the coordinate system is rotated in a like manner as the view.

Like prior art DMA or CIMA analyzers, cross-flow mobility analyzer 4 comprises two parallel plates 14 and 24 defining a volume between them and gas (represented by arrows 10) flowing parallel to an axis (the y-axis). Unlike prior art DMA or CIMA analyzers, plates 14 and 24 are not apertured, but are substantially solid. That is, although plates 14 and 24 may be composed of a multitude of components, the combined components present a solid surface. Interior surfaces of plates 14 and 24 are smooth so as to support a laminar gas flow. Further, unlike prior art DMA or CIMA analyzers, plates 14 and 24 are constructed so as to support both an RF confining field—represented by arrows 12—and a DC electrostatic analytical field—represented by arrows 20—in the volume between the plates.

Also, unlike prior art DMA analyzers, analyte ions are not introduced into or extracted from analyzer 4 via apertures in plates 14 and 24. Rather, ions are introduced along an axis orthogonal to analytical gas flow 10 and parallel to the surface of the plates (i.e. ions are introduced along the z-axis). The path of the ions is represented by crossed circle 8 in FIG. 2A and by arrow 6 in FIG. 2B. Notice that crossed circle 8 and arrow 6 represent the same ion path. An RF pseudopotential, represented by arrows 12, tends to confine ions in at least one dimension—i.e. in the x-dimension—but does not significantly hinder the motion of the ions along the z-axis. Means and methods for such pseudopotential fields are well known in the prior art. For example, such means and methods are described by Franzen in U.S. Pat. No. 5,572,035, incorporated herein in its entirety by reference, entitled "Method and device for the reflection of charged particles on surfaces".

Although only two arrows are drawn in FIG. 2A representing RF pseudopotential 12, it is assumed that the field is homogeneous—i.e. the strength of the pseudopotential does not vary substantially with y or z position. In alternate embodiments, the pseudopotential may vary with y position. The strength of analytical electric field 20 is substantially homogeneous and not a function of x or y. In alternate embodiments, the analytical field may be a function of either x or y position. Gas flow 10 is substantially laminar and in the form of a parabolic velocity profile—i.e. gas flow velocity is a parabolic function of x. However, gas flow 10 does not vary significantly with y or z. In alternate embodiments, gas flow 10 may vary widely in pressure, number density, and flow velocity as a function of x or y position. In still other alternate embodiments gas flow has a "plug" rather than parabolic flow profile. Neither the analytical field 20 nor the gas flow 10 varies significantly with z position.

In alternate embodiments analyzer 4 may include entrance, exit, and analytical regions. In such embodiments, the analytical region is a central region—i.e. central along the z-axis. Importantly, the analytical region has substantially ideal RF and analytical fields and a substantially ideal gas flow—i.e. ideal for the purpose of mobility analysis. The analytical region is bounded by entrance and exit regions—i.e. via which ions enter and exit the analyzer. The RF and analytical fields and the gas flow in the entrance and exit regions may be non-ideal—for example, to assist the injection or extraction of ions. In further alternate embodiments, plates 14 and 24 may be apertured and/or may have rough surfaces. In other alternate embodiments, ions may be introduced into analyzer 4 via such apertures.

Along the y-axis, the drag force induced on the ions by gas flow 10 is counteracted by DC analytical field 20. From first principles, the velocity of an ion in a gas stream is given by the product of the ion's mobility and the strength of the electrical field—i.e. the DC analytical field. Thus, providing a gas flow 10 of known velocity and a DC analytical field 20 of known strength will define the mobility ions must have in order to stably move along path 6. Scanning the DC analytical field strength and/or the analytical gas flow velocity will similarly scan the mobility of the ions that can be transmitted along path 6. Ions of lower mobility—i.e. lower than the selected mobility—will be pushed by the gas off of path 6 towards higher y values. Ions of higher mobility—i.e. higher than the selected mobility—will be pushed by the analytical field 20 off of path 6 towards more negative y-positions.

The cross-flow ion mobility analyzer according to the present invention may be used in conjunction with any known ion production method including laser desorption (LD), matrix assisted laser desorption ionization (MALDI), electrospray ionization (ESI), chemical ionization (CI), photoionization (PI), or any other known method of producing ions. The cross-flow mobility analyzer is a filter-type analyzer.

Thus, when using a continuous ionization source such as ESI, a continuous beam of ions of the selected mobility will be produced at the exit of the cross-flow mobility analyzer. By scanning the strength of the DC analytical field 20, the mobility of the transmitted ion beam can be scanned. Recording the intensity of the resultant ion beam while scanning the strength of the field 20 will yield an ion mobility spectrum. Recording a series of mass spectra from the resultant ion beam while scanning the strength of the analysis field 20 will result in an ion mobility—mass spectrum.

As mentioned above RF confining field 12 tends to prevent ions from diffusing away along the x-axis, however, ions of the selected mobility may diffuse along the y or z axes. Diffusion along the z-axis will tend to bring some of the selected ions to the ion outlet (exit) of the device whereas diffusion along the y-axis will cause the ions to be lost. In alternate embodiments a weak pseudopotential confining field along the y-axis is used to prevent ions of the desired mobility from diffusing away along the y-axis.

In alternate embodiments the electric fields are produced via elements which are not integrated with plates 14 and 24. Rather, plates 14 and 24 define a gas flow while independent electrodes are used to produce the electric fields. In further alternate embodiments the strength of DC analytical field 20 varies along the y-axis so that ions of the mobility of interest are confined in the y-dimension to path 6. For example, DC analytical field 20 may increase with y-position such that if ions of the selected mobility move to higher y-positions—e.g. by diffusion, the DC analytical field—having a greater strength at such higher y-position—will push the ion back toward path 6. Conversely, if ions of the selected mobility move to lower y-positions, DC analytical field 20 will be too weak to hold the ions in position against gas flow 10 and the ions will be pushed back towards path 6. In alternate embodiments the gas flow is reduced as a function of position along the y-axis so that ions of the selected mobility are similarly confined in the y-dimension to path 6.

Turning next to FIGS. 3A-3D, alternate embodiment cross-flow mobility analyzer 94 is shown. Analyzer 94 is composed of abridged quadrupole 84, inlet capillary 60, exit skimmer 62, a gas supply (not shown) for generating the analytical gas flow, and power supplies (not shown) for generating the RF confining potentials, the DC analytical potentials, and potentials applied to the inlet capillary and exit skimmer. Abridged quadrupole 84 is comprised of two parallel plates 184 and 284, each constructed so as to support both an abridged quadrupolar RF confining field and a homogeneous dipolar analysis field in the volume between the plates.

According to the present embodiment, each of plates 184 and 284 are constructed of an insulating support with resistive and conducting films deposited on its surface. FIG. 3A shows an end view of insulating support 92 used in the construction of abridged quadrupole 84 depicted in FIGS. 3C and 3D. Insulating support 92 may be comprised of any electrically insulating material, however, as an example, insulating support 92 is comprised of ceramic. Support 92 has a length which is the same as that of abridged quadrupole 84. Although any insulating material may be used to make support 92, ceramic is especially advantageous in that it is hard and rigid. As shown in FIG. 3A, the cross section of support 92 has the form of an isosceles trapezoid with legs 85 and 86 having a 45 degree angle with respect to base 87 and a 135 degree angle with respect to base 88. A wide variety of dimensions may be chosen for support 92, however, as an example, base 88 is 10.8 mm long (i.e. along the y-axis). Support 92 is 1 mm thick and 50 mm long (i.e. along the x and z axes respectively).

As depicted in FIG. 3B, plate 184 is constructed using support 92 with resistive and conducting films deposited on surface 88. The patterning of the conducting film on surface 88 produces a set of regularly spaced electrodes 90 represented in FIG. 3B as white space. Resistive film 89 is represented by shaded regions between the electrodes. The thicknesses of the resistive and conductive films may be chosen to be any thickness—even to the extent that, for example, support 92 is replaced by bulk resistive material (for example, graphite doped polymer). However, in the example of FIG. 3, the films are between $10^{-10}$ and $10^{-5}$ m thick. Resistive film 89 may be comprised of any known electrically resistive material, however, as an example, resistive film 89 is comprised of a metal oxide such as tin oxide. Preferably, the resistance of resistive layer 89 is uniform across surface 88, however, in alternate embodiments, the resistance of layer 89 may be non-uniform along the length or width of surface 88. The conductive film used to produce electrodes 90 may be comprised of any electrically conducting material, however as an example, electrodes 90 are comprised of a metal, such as gold. Resistive layer 89 is bounded by, and in electrical contact with, electrodes 90. Alternatively electrodes 90 are deposited on top of resistive layer 89

In alternate embodiments, support 92 may be comprised of glass—for example, the type of glass used in the production of microchannel plate detectors (Photonis Inc., Sturbridge, Mass.). Resistive layers may be formed on the surface of such glass by reduction in a hydrogen atmosphere.

As shown in FIGS. 3C and 3D, abridged quadrupole 84 is constructed using plates 184 and 284. Each of these plates is constructed in the manner described above with respect to plate 184, having supports and resistive and conductive films. The surface 88 and 93 of plates 184 and 284 respectively having resistive and conductive coatings thereon are assembled into analyzer 94 so that they are parallel to each other and facing the ion path—i.e. the z-axis. The gap between plates 184 and 284—i.e. along the x axis—may vary widely, however, as an example, the distance between the plates is 3.6 mm. In the preferred embodiment, the resistance of the coating on plate 184 is identical to that on plate 284. In alternate embodiments, the resistance of the coating may differ from one plate to another.

An electric field consisting of the superposition of a quadrupolar RF confining field and a homogeneous dipole analytical field can be formed in abridged quadrupole 84 by applying potentials to electrodes 90 on plates 184 and 284 in accordance with equation (1). The quadrupolar RF component of the field results in a pseudopotential which tends to radially focus the ions to path 26 in a similar manner as described above with respect to pseudopotential 12. The dipole component of the field acts as an analytical field in a similar manner as described above with reference to analytical field 20.

According to the present embodiment, there are three modes of operation—"transmission", "mass analysis", and "mobility analysis" modes. In transmission mode, abridged quadrupole 84 is operated with a quadrupolar RF confining field but no dipole analytical field. Also, no analytical gas flow is present when operating in transmission mode. Inasmuch as there is only an RF field that confines ions to path 26, ions of a wide range of masses may pass unhindered from inlet capillary 60 to exit skimmer 62. In transmission mode, the range of masses which are transmitted can be tuned via the strength of the RF field as is well known from the prior art.

In mass analysis mode, ions are selected according to mass by adding a DC bias, U, to the quadrupolar field (see equation (2)). This sort of mass selective stability is also known from the prior art. Using a quadrupolar RF field of a predetermined RF amplitude, V, and frequency, f, and by applying a DC bias, U, of a predetermined magnitude, ions of only a selected mass or mass range will be transmitted from inlet capillary 60 to exit skimmer 62.

To mobility analyze ions, DC bias, U, is set to zero volts. An analytical gas flow is established along the y-axis, and an analytical dipole field—i.e. Ey in equation (1)—is applied in opposition to the gas. As discussed above with reference to FIG. 2, the drag force induced on the ions by the analytical gas flow along the y-axis is counteracted by the DC analytical field component, Ey. From first principles, the velocity of an ion in a gas stream is given by the product of the ion's mobility and the strength of the electrical field, Ey. Thus, providing an analytical gas flow of known velocity and an analytical field, Ey, of known strength defines the mobility ions must have in order to pass stably through the analyzer. Scanning the DC analytical field strength will similarly scan the mobility of the ions that are transmitted through the analyzer. Ions of lower mobility—i.e. lower than the selected mobility—will be pushed by the gas towards higher y values, while ions of higher mobility will be pushed by the analytical field towards more negative y-positions.

Importantly, the Bore of Capillary 60 and the Aperture of Skimmer 62 are located at y=0. Thus, ions from the capillary are introduced into analyzer 94 at y=0.

The selected mobility ions move stably along path 26 at y=0 and then exit analyzer 94 via the aperture in skimmer 62 at y=0. Thus, ions that are pushed to higher or lower y-positions will substantially not pass through the aperture in skimmer 62 and will therefore be lost.

It is worth noting that ions may be introduced via capillary 60 as part of a gas stream. A gas flow from capillary 60 as well as a repulsive electric potential on capillary 60 may be used to eject ions from the capillary and into analyzer 94. Similarly, there may be some amount of gas flow out of analyzer 94 via the aperture in skimmer 62. Such a gas flow as well as an attractive potential on skimmer 62 may be used to extract ions out of analyzer 94 and direct them towards downstream optics, mass or mobility analyzers, or detectors.

In alternate embodiments, the pressure, composition, and velocity of analytical gas may vary widely, however, as an example, the pressure, composition, and velocity of the analytical gas are 3 mbar of nitrogen and 15 m/s respectively. In alternate embodiment methods, the analytical field strength may vary widely, however, as an example, the field strength, $E_y$, may be 0-30 V/cm. In embodiments with confining and analytical field being DC fields, the pressure of the analytical gas can be much higher than 10 mbar and may even be equal to atmospheric pressure.

Under certain conditions, the pseudopotential restoring force on an ion in a quadrupolar RF field can be expressed as:

$$F_x = -bx/m \quad (3)$$

$$F_y = -by/m \quad (4)$$

where $F_x$ and $F_y$ are the forces on the ion along the x and y axes respectively, b is a constant, and m is the mass of the ion. Clearly, from equation (3) the force, $F_x$, along the x-axis will tend to focus the ions onto the z-axis and therefore path 26. The focusing of ions via force $F_x$ will not be significantly influenced by the analytical dipole field, $E_y$, or the drag force from the analytical gas flow, because neither of these has a component along the x-axis.

However, the y-position that ions assume during a cross-flow mobility analysis will be dependent on the analytical dipole field, $E_y$, the drag force on the ions due to the analytical gas flow, and the pseudopotential restoring force $F_y$. An equilibrium y-position of an ion will be established at a point where the net force along the y-axis, $F_{net}$, is zero:

$$F_{net} = 0 = F_K + F_y + F_E \quad (5)$$

where $F_K$ is the drag force on the ion due to the gas flow (associated with the ion's mobility), $F_y$ is the restoring pseudopotential force on the ion due to the abridged RF quadrupole field, and $F_E$ is the force on the ion due to the analytical dipole field. For the purpose of estimating the behavior of ions in the analyzer according to the present invention, one may assume that the ions are roughly spherical with a volume proportional to the mass of the ion. If this were true, then the drag force on the ion due to the gas flow would be:

$$F_K = a\,v\,m^{2/3} \quad (6)$$

where "a" is a constant, and v is the velocity of the gas. At the selected mobility, the drag force $F_K$ will be counterbalanced by the force due to the analytical dipole field $F_E = qE_y$, and the net force on the ion will be given by the pseudopotential restoring force $F_y$ alone. Thus, ions of the selected mobility will be confined to path 26—i.e. the z-axis.

Notice that the diffusion of ions away from path 26 will be counteracted by the pseudopotential force, $F_x$ and $F_y$. Thus, the selected mobility ions will be transmitted with high efficiency. Ions of other mobilities will take up y-positions roughly given by:

$$y = m/b(avm^{2/3} - qE_y) \quad (7)$$

one implication being that at very low mass, the equilibrium position of the ion, y, approaches zero, and the ion may theoretically follow path 26. However, ions of very low mass will be unstable in the RF quadrupole field—i.e. they will be below the low mass cutoff—and will be ejected laterally into one of plates 184 or 284. Thus, only ions of the selected mobility will follow path 26.

It is interesting to note that the constant "a" in equations (6) and (7) encompasses parameters important to ion mobility such as gas pressure, and temperature. Similarly, "b" in equation (4) and (7) encompasses parameters important to the RF quadrupolar pseudopotential such as RF frequency, and amplitude. By adjusting the gas pressure and/or velocity, the RF frequency or amplitude, or the dipole electric field strength, for example, one can adjust the y-position dependence on the ion mobility. For example, increasing the velocity, v, of the analytical gas will tend to increase the change in y-position of ions with their mobility—i.e. dy/dK increases with increasing gas velocity, v. Because the ions are more separated on the y-axis according to mobility, this will tend to result in a higher resolution. Similarly, reducing "b"—by, for example, reducing the amplitude of the RF quadrupole field—will tend to spread the ions out according to mobility along the y-axis and therefore increase mobility resolution. In general, the optimum mobility performance will be obtained when using the largest possible value of "a" and the smallest possible value of "b" that still confines the selected mobility ions to path 26.

In alternate embodiments, a mixed mode of mass and mobility analysis may be achieved by simultaneously setting a non-zero DC bias, U, and providing an analytical gas flow along the y-axis and an analytical dipole field in opposition to the analytical gas flow. In such a "mixed mode" only ions within a predetermined narrow mass range and of a given mobility or mobility range will be transmitted through the analyzer.

As discussed above, ions may progress through analyzer 94 from capillary 60 to skimmer 62, for example, by diffusion. Furthermore, the Coulombic interaction of downstream ions with upstream ions will tend to force the downstream ions toward skimmer 62. As discussed in part above, in alternate embodiments ions may be forced from entrance end to exit via an axial RF or DC field (i.e. along z-axis). Such axial field may be formed by any prior art means. In one alternate embodiment mentioned above a DC potential applied to angled wires, foils, or plates will produce a field component along the z-axis so as to force the ions along the axis. In other alternate embodiments, an axial pseudopotential may be produced by, for example, placing plates 184 and 284 in the analyzer assembly at an angle with respect to one another. That is, the gap (along the x-axis) between the plates would be greater at the exit end of the analyzer—i.e. near skimmer 62—than the entrance end—i.e. near capillary 60. The axial component of the pseudopotential would, of course, push ions through the analyzer. In yet a further alternate embodiment, the analytical gas flow has a velocity component along the z-axis. This z-axis velocity component in the gas flow will force the ions to progress through the analyzer at a well determined rate—independent of the ions' mobility or mass.

Any other parameter in the instrument may be scanned while scanning the strength of the DC analysis field. For example, the strength of the RF field, V, may be scanned with the strength of the DC analysis field, Ey. By increasing the RF field strength with the analysis field strength, one may improve ion transmission. That is, at low analysis field strengths, Ey, ions of high mobility will be transmitted. Ions of high mobility tend to be of low mass. Low mass ions require a low RF field strength, V, in order to avoid a "low mass cutoff". However, at high analysis field strengths, ions of low mobility—corresponding to generally higher mass— will be transmitted. Ions of such high mass will generally be more effectively transmitted when using a high RF field strength. In addition, when used in conjunction with a quadrupole mass filter, one might link the settings of—and thereby the mass of the ions transmitted by—the quadrupole mass filter with DC analysis field strength, Ey. For example, at higher analysis field strengths (transmitting lower mobility ions) one might transmit higher mass species through the quadrupole mass filter.

In alternate embodiments, an additional pair of wires may be positioned parallel to the z-axis (longitudinal axis) one each at, for example, x=0, y=+/−1 mm such that ions deviating from the z-axis by more than +/−1 mm will collide with the wires and be eliminated. FIG. 4 depicts an alternative embodiment cross-flow mobility analyzer identical to analyzer 94 with the exception that conducting wires 96 and 97 have been added at y=+/−1 mm. The diameter, length, and placement of the wires may vary widely, however, as an example, the wires are 0.12 mm in diameter, 20 mm in length, and placed, lengthwise, in the center of analyzer 95. Notice from equation (1) that the RF component of the electric field is zero at x=0. Thus, only a DC potential needs to be applied—i.e. Ey—to the wires. In further alternate embodiments, the wires may be placed at any desired y-position. In further alternate embodiments, the wires are replaced with conducting plates which are placed in the y—z plane having their nearest edges at, for example, +/−1-1 mm. In further alternate embodiments, the wires are angled so as to produce an axial field (i.e. along the z-axis) that pushes the ions from the inlet capillary towards the exit skimmer.

The wires need not cover the entire length of analyzer. Rather, as depicted in FIG. 4A, wires 96 and 97 extend the length of central analytical region 32 of the analyzer 95. Analyzer 95 includes entrance, exit, and analytical regions, 31, 32, and 33 respectively. In the entrance and exit regions, the analytical gas flow and/or the electric fields may be disturbed by, for example, the presence of capillary 60 or exit skimmer 62. Thus, ions may not find their equilibrium y-positions—i.e. as described by equation (7)—while in the vicinity of the capillary inlet or exit skimmer. Having the above mentioned wires absent from the vicinity of the capillary inlet and exit skimmer allows ions to deviate from their expected positions until they enter analytical region 32 wherein the gas flow is uniform and the electric fields are near ideal. Ions far from path 26 in the analytical region will then encounter wires 96 or 97 and be eliminated.

FIG. 5 depicts a further alternate embodiment cross-flow mobility analyzer 98. Analyzer 98 is identical to analyzer 94 of FIG. 3 except for the addition of conducting foils 41 and 42 used as structural elements to disturb the parabolic velocity profile and form a plug flow along the longitudinal axis (z-axis). The dimensions and placement of foils 41 and 42 may vary widely, however, as an example, the foils are 0.12 mm thick, 2 mm high (along the y—axis), and cover the entire length of the analyzer (along the z—axis). Foils are spaced equally along the x—axis with their interior facing edges at y=+/−1.75 mm as depicted in FIG. 5B. An analytical gas flow is introduced along the y—axis between plates 184 and 284. As is well known from the prior art, the presence of foils 41 and 42 will tend to cause the analytical gas stream to adopt a plug flow in the vicinity of path 26. The analytical gas flow may be introduced, for example, from the bottom of the analyzer—i.e. through foils 42. In such case, the upper set of foils 41 are not necessary for producing a plug flow but may be useful for maintaining a symmetric analytical DC field and RF confining field.

Potentials are applied to foils 41 and 42 in a manner consistent with that described with reference to FIG. 3. In particular, an electric field consisting of the superposition of a quadrupolar RF confining field and a homogeneous dipole analytical field is formed in analyzer 98 by applying potentials to foils 41 and 42, and electrodes 90 on plates 184 and 284 in accordance with equation (1). The quadrupolar RF component of the field results in a pseudopotential which tends to focus the ions to path 26. The dipole component, $E_y$, of the field acts as the DC analytical field. The potentials on the interior facing edge of foils 41 and 42—i.e. that surface having the minimum absolute value of y—are most relevant for generating the field. That is, the potentials on foils 41 & 42 are set based on equation (1) using the x and y positions of their interior facing edges.

The further operation and modes of operation—i.e. ion guide, mass filter, and mobility filter—of analyzer 98 are the same as those of analyzer 94 as described with reference to FIG. 3. In alternate embodiments, an additional pair of wires may be positioned parallel to the z-axis one each at, for example, x=0, y=+/−1 mm such that ions deviating from the z-axis by more than +/−1 mm will collide with the wires and be eliminated. As described with reference to FIG. 4, the wires need not cover the entire length of the analyzer, rather, the analyzer may be divided into sections with the added wires covering only a central analytical section.

Figure 6:
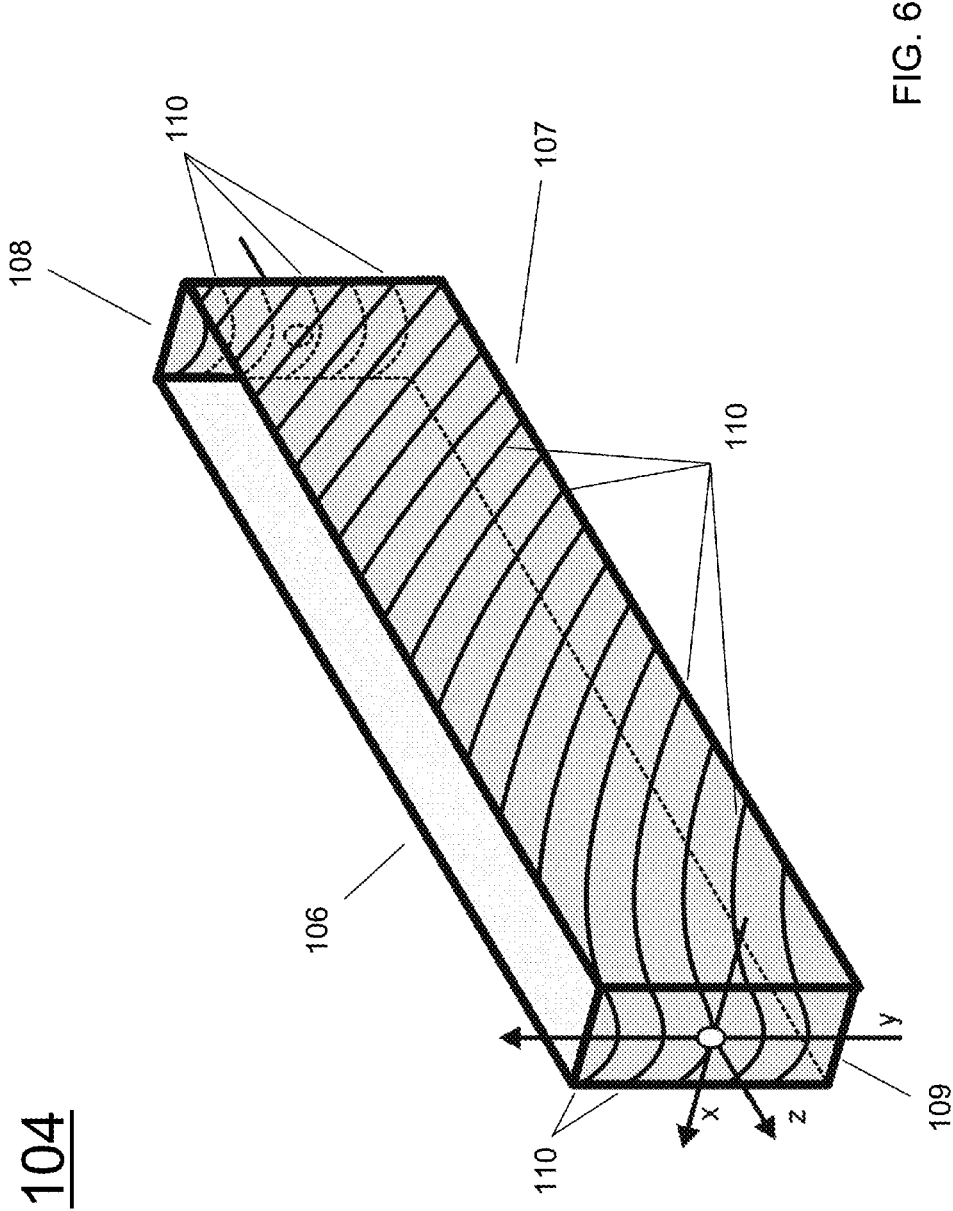
FIG. 6 depicts a cross-flow mobility according to the present invention constructed so as to support a DC electric field having a first component which focuses ions in the x-dimension and a second component which acts as the analytical field.

In a further alternate embodiment depicted in FIG. 6, the electric field is comprised of only a DC component and no RF component. A first component of the electric field focuses ions in the x-dimension toward the z-axis. Simultaneously a second component of the electric field acts as the analytical field—i.e. along the y-axis. As described with respect to the previous embodiments above, alternate embodiment cross-flow mobility analyzer 104 is comprised of plates 106 to 109 defining a volume through which the analytical gas can flow. Apertured plates 108 and 109 are positioned at entrance and exit ends respectively of analyzer 104. As depicted in FIG. 6, the apertures in plates 108 and 109 are positioned on the z-axis such that selected ions enter through the aperture in plate 108, travel along the z-axis, and exit the analyzer through the aperture in plate 109. In alternate embodiments, ions may be injected into and extracted from the analyzer via any known means. In alternate embodiments, plates 108 and 109 may, for example, be replaced with a capillary and a skimmer.

Each of plates 106-109 comprise electrodes 110 (shown as curves in FIG. 6) which are supplied with DC potentials. Electrodes 110 and the DC potentials applied thereto produce an electric field in the volume of analyzer 104 given by:

$$\Phi(x, y, z, t) = \frac{\Phi_0(x^2 - z^2)}{r_o^2} + E_y(t) \cdot y + \chi \cdot z \quad (8)$$

where $\Phi_0$ is a DC potential, $E_y(t)$ is a function of time relating to an adjustable DC analytical field, $r_o$ is a constant, and x and y are orthogonal coordinates, and z is the coordinate along the longitudinal axis. The field component $(\Phi_0/r_o)x^2$ relates to a confining field along the x-axis. The field components—$(\Phi_0/r_o) z^2 + \chi \cdot z$ (with constant $\chi$) relate to axial DC fields along the z-axis. Plates 106-109 may be constructed in a similar manner as that described with respect to plate 184 above—i.e. resistive and conductive films on an insulating support—however, electrodes 110 are not simple lines parallel to the z-axis as implied by equation (1), rather, electrodes 110 follow curves indicative of equation (8).

During operation, analytical gas flows through the volume of analyzer 104 in the y-direction—for example from bottom to top. Ions introduced at the inlet aperture in plate 108, are confined along the x-direction, and experience a constant electric field in the y-direction which counteracts the drag force on the ions due to the gas flow. The z-component of the electric field increases along the z-direction and drives the ions through the volume towards plate 109 and the analyzer exit.

Figure 7:
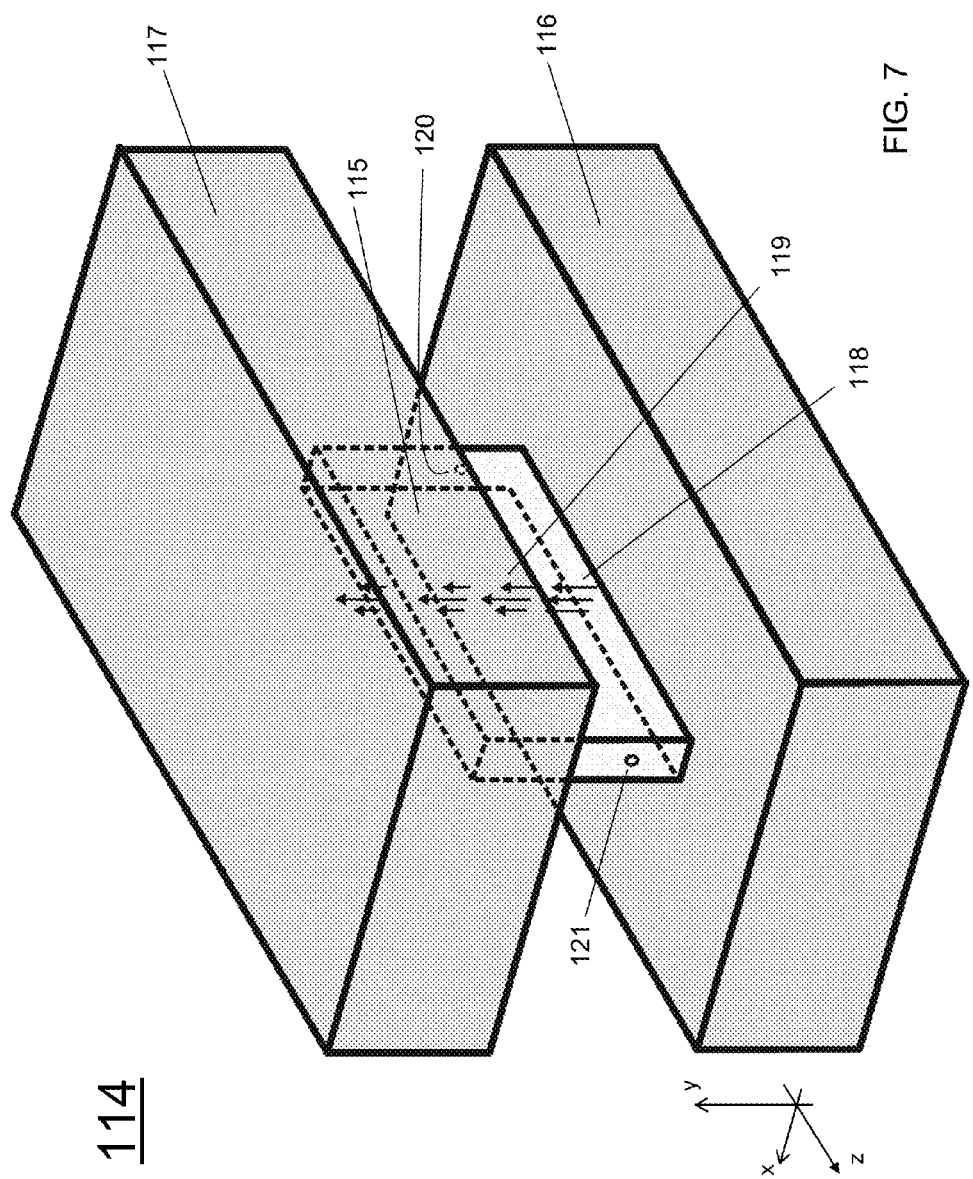
FIG. 7, shows gas reservoirs and the interior volume of a cross-flow mobility analyzer according to the present invention.
Figure 8:
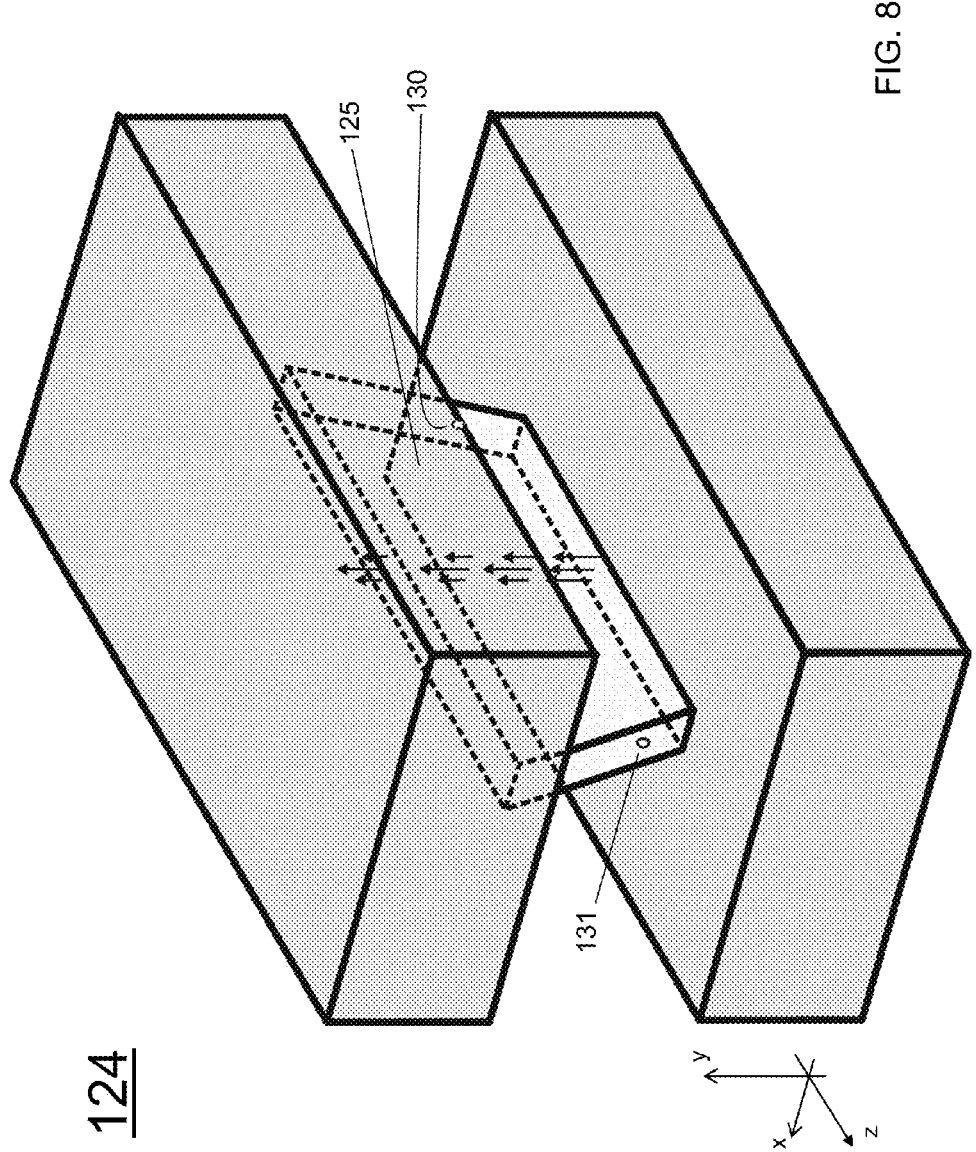
FIG. 8 depicts the interior volume of a cross-flow mobility analyzer and associated gas reservoirs wherein the volume opens along the analytical direction.

In embodiment 114 of FIG. 7, only the interior volume 115 of a cross-flow mobility analyzer according to the present invention as well as gas reservoirs 116 and 117 are shown. For the sake of clarity all plates and electrodes are not shown. During operation, the gas pressure in reservoir 116 is higher than that in reservoir 117. The pressure difference between the reservoirs generates a parabolic gas flow through volume 115 as represented by arrows 119. However, the parabolic flow profile is not well established near reservoir 116, rather the profile is closer to a plug flow as represented by arrows 118. Thus, in embodiment 114, ion inlet 120 and outlet 121 are located near the inflow of volume 115—i.e. near reservoir 116, so that the analytical gas velocity profile is near the plug flow region. As a result, the analytical gas flow velocity is in particular substantially independent of x and z position when near the z-axis. Thus, the mobility selection of ions is not strongly dependent on their x-position in the analyzer and mobility resolution is improved. Alternate embodiment 124 of FIG. 8 is the same as that described with reference to FIG. 7 except that volume 125 opens along the analytical direction—i.e. along the y-axis. Such a geometry tends to extend the plug flow region at least along the z-axis and generates an even more homogeneous velocity profile on the axis between inlet 130 and outlet 131.

The cross-flow ion mobility analyzer according to the present invention may be used without subsequent mass analysis. That is, ions may be detected following the mobility analysis without any further manipulation by other ion optical devices. In the same vein, in alternate embodiments, the cross-flow ion mobility analyzer according to the present invention may be built and used as a stand-alone device. That is, the mobility analyzer according to the present invention may be the only analyzer in alternate embodiment instruments. Alternatively, the mobility analyzer may be incorporated in instruments having any number of other mobility and/or mass analyzers including a quadrupole filter, a time-of-flight mass analyzer, an ion cyclotron resonance mass analyzer, a Paul trap, an orbitrap, or any combination of such analyzers.

While the present invention has been described with reference to one or more preferred and alternate embodiments, such embodiments are merely exemplary and are not intended to be limiting or to represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. An apparatus for the mobility analysis of ions comprising:
    means for generating a first and second electric field in a volume in a manner so that the first electric field confines ions to a longitudinal axis along at least one direction orthogonal to the said axis and the second electric field is a DC field orthogonal to the longitudinal axis; and
    a duct forming a gas flow path in the volume, the gas flow having a velocity component orthogonal to the longitudinal axis so that a first force generated on the ions by the DC field counteracts a second force generated on the ions by the orthogonal velocity component of the gas flow.

2. The apparatus of claim 1 wherein the duct is a cylinder having a gas entrance opening located on one side of the longitudinal axis and a gas exit opening located at an opposite side of the longitudinal axis, the cylinder being laterally closed along the path of the gas flow except for an ion inlet located where the longitudinal axis intersects one end of the cylinder and an ion outlet located where the longitudinal axis intersects an other end of the cylinder.

3. The apparatus according to claim 2 wherein the gas flow has a parabolic velocity profile within the cylinder and the apparatus comprises structural elements are positioned inside the cylinder in a manner that disturbs the parabolic velocity profile within the cylinder to produce a plug gas flow region near one of the gas entrance opening or a recess of the cylinder.

4. The apparatus according to claim 2 wherein the ion inlet and the ion outlet are located in the plug gas flow region.

5. The apparatus according to claim 2 wherein the orthogonal velocity component of the gas flow has a parabolic profile along the longitudinal axis and wherein the counteracting DC field has a parabolic field strength profile along the longitudinal axis and/or is generated only near the apex region of the parabolic profile.

6. The apparatus according to claim 2 wherein the orthogonal velocity component of the gas flow has a parabolic profile along the longitudinal axis and wherein the counteracting DC field is generated only near an apex region of the parabolic profile.

7. The apparatus according to claim 1 wherein the duct is formed by two parallel plates positioned about the longitudinal axis so that the path of the gas flow is oriented parallel to the surface of said plates and the ion path is positioned symmetrically between the plates.

8. The apparatus according to claim 1 wherein the duct forming the path for the gas flow is oriented orthogonally to the longitudinal axis.

9. The apparatus according to claim 1 wherein the means for generating the electric fields comprises a set of electrodes connected to an RF voltage supply and to a DC voltage supply wherein the first electric field is an RF electric field which radially confines the ions on the longitudinal axis.

10. The apparatus according to claim 9, wherein set of electrodes are arranged rectilinearly and symmetrically about the longitudinal axis generating an electric field inside the volume having the form:

$$\Phi(x, y, t) = \frac{\Phi_o(t) \cdot x \cdot y}{2r_o^2} + E_x(t) \cdot x + E_y(t) \cdot y$$

where $\Phi_o(t)$ is an RF potential, $E_x(t)$ and $E_y(t)$ are functions of time relating to an adjustable homogeneous DC field, $r_o$ is a constant, and x and y are orthogonal coordinates.

11. The apparatus according to claim 10 further comprising filtering electrodes placed parallel to and on opposite sides of the longitudinal axis.

12. The apparatus according to claim 1 wherein the means for generating the electric fields comprise a set of electrodes connected to a DC voltage supply and the first electric field is an electric DC field confining the ions only along one orthogonal direction to the longitudinal axis, the confining direction being orthogonal to the second electric DC field.

13. The apparatus according to claim 12 wherein the electric field inside the volume has the form:

$$\Phi(x, y, z, t) = \frac{\Phi_0(x^2 - z^2)}{r_o^2} + E_y(t) \cdot y$$

where $\Phi_0$ is a DC potential, $E_y$ is a function of time relating to an adjustable DC field, $r_o$ is a constant, and x and y are orthogonal coordinates, and z is the coordinate along the longitudinal axis.

14. An apparatus for the mobility—mass analysis of ions comprising:
an ion source;
a cross-flow mobility analyzer comprising means for generating a first and second electric field in a volume in a manner so that the first electric field confines ions to a longitudinal axis along at least one direction orthogonal to the said axis and the second electric field is a DC field orthogonal to the longitudinal axis and a duct forming a gas flow path in the volume, the gas flow having a velocity component orthogonal to the longitudinal axis so that a first force generated on the ions by the DC field counteracts a second force generated on the ions by the orthogonal velocity component of the gas flow; and
a mass analyzer.

\* \* \* \* \*